(12) United States Patent
Okada et al.

(10) Patent No.: US 8,486,911 B2
(45) Date of Patent: Jul. 16, 2013

(54) TH1-ASSOCIATED MICRORNAS AND THEIR USE FOR TUMOR IMMUNOTHERAPY

(75) Inventors: Hideho Okada, Pittsburgh, PA (US); Gary Kohanbash, Pittsburgh, PA (US); Kotaro Sasaki, Pittsburgh, PA (US)

(73) Assignee: University of Pittsburgh—Of the Commonwealth System of Higher Education, Pittsburgh, PA (US)

( * ) Notice: Subject to any disclaimer, the term of this patent is extended or adjusted under 35 U.S.C. 154(b) by 0 days.

(21) Appl. No.: 13/568,457

(22) Filed: Aug. 7, 2012

(65) Prior Publication Data

US 2012/0301448 A1 Nov. 29, 2012

Related U.S. Application Data

(63) Continuation of application No. 12/818,016, filed on Jun. 17, 2010.

(60) Provisional application No. 61/187,903, filed on Jun. 17, 2009.

(51) Int. Cl.
*A01N 43/04* (2006.01)
*A61K 31/70* (2006.01)

(52) U.S. Cl.
USPC ..................................... 514/44 A; 514/44 R

(58) Field of Classification Search
None
See application file for complete search history.

(56) References Cited

U.S. PATENT DOCUMENTS

| 2007/0072204 A1 | 3/2007 | Hannon et al. |
| 2008/0306006 A1 | 12/2008 | Croce et al. |
| 2009/0062224 A1 | 3/2009 | Kim et al. |

FOREIGN PATENT DOCUMENTS

| WO | WO 2006/119365 A2 | 11/2006 |
| WO | WO 2006/137941 | 12/2006 |
| WO | WO 2008/014008 | 1/2008 |
| WO | WO 2008/057234 A2 | 5/2008 |
| WO | WO 2008/070082 | 6/2008 |

OTHER PUBLICATIONS

Banerjee et al., "Micro-RNA-155 inhibits IFN-γ signaling in CD4+T cells," *Eur. J. Immunol.* 40:225-231, 2010.
Brock et al., "Interleukin-6 Modulates the Expression of the Bone Morphogenic Protein Receptor Type II Through a Novel STAT3-microRNA Cluster 17/92 Pathway," *Circ Res*, 104:1184-1191, 2009.
Chen et al., "MicroRNAs Modulate Hematopoietic Lineage Differentiation," *Science*, 303:83-86, 2004.
Costinean et al., "Pre-B Cell Proliferation and Lymphoblastic Leukemia/High-Grade Lymphoma in Eµ-miR155 Transgenic Mice," *Proc Natl Acad Sci USA*, 103:7024-7029, 2006.
Dews et al., "Augmentation of Tumor Angiogenesis by a Myc-Activated microRNA Cluster," *Nat Genet*, 38:1060-1065, 2006.
Dostie et al., "Numerous microRNPs in Neuronal Cells Containing Novel microRNAs," *RNA*, 9:180-186, 2003.
Eis et al., "Accumulation of miR-155 and BIC RNA in Human B Cell Lymphomas," *Proc Natl Acad Sci USA*, 102:3627-3632, 2005.
Hayashita et al., "A Polycistronic MicroRNA Cluster, miR-17-92, is Overexpressed in Human Lung Cancers and Enhances Cell Proliferation," *Cancer Res*, 65:9628-9632, 2005.
He et al., "A microRNA Polycistron as a Potential Human Oncogene," *Nature*, 435:828-833, 2005.
Inomata et al., "MicroRNA-17-92 Down-Regulates Expression of Distinct Targets in Different B-Cell Lymphoma Subtypes," *Blood*, 113:396-402, 2009.
Lawrie, "MicroRNA Expression in Lymphoma," *Expert Opin Biol Ther*, 7:1363-1374, 2007.
Li et al., "miR-181a Is an Intrinsic Modulator of T Cell Sensitivity and Selection," *Cell*, 129:147-161, 2007.
Lim et al., "Vertebrate MicroRNA Genes," *Science*, 299:1540, 2003.
Matsubara et al., "Apoptosis Induction by Antisense Oligonucleotides Against *miR-17-5p* and *miR-20a* in Lung Cancers Overexpressing *miR-17-92*," *Oncogene*, 26:6099-6105, 2007.
Mendell, "miRiad Roles for the miR-17-92 Cluster in Development and Disease," *Cell*, 133:217-222, 2008.
Nagel et al., "Activation of miR-17-92 by NK-like Homeodomain Proteins Suppresses Apoptosis via Reduction of E2F1 in T-cell Acute Lymphoblastic Leukemia," *Leukemia &Lymphoma*, vol. 50(1):101-108, 2009.
Northcott et al., "The miR-17/92 Polycistron Is Up-Regulated in Sonic Hedgehog-Driven Medulloblastomas and Induced by N-myc in Sonic Hedgehog-Treated Cerebellar Neural Precursors," *Cancer Res*, 69:3249-3255, 2009.
O'Connell et al., "Sustained Expression of microRNA-155 in Hematopoietic Stem Cells Causes a Myeloproliferative Disorder," *J Exp Med*, 205:585-894, 2008.
O'Donnell et al., "c-Myc-Regulated microRNAs Modulate E2F1 Expression," *Nature*, 435:839-843, 2005.
Okada et al., "MicroRNAs in Immune Regulation—Opportunities for Cancer Immunotherapy," *Int J Biochem Cell Biol*, 42:1256-1261, 2010.

(Continued)

*Primary Examiner* — Jennifer Pitrak McDonald
(74) *Attorney, Agent, or Firm* — Klarquist Sparkman, LLP

(57) ABSTRACT

Described herein is the identification of miRNAs (miRs) that are up-regulated in Th1 cells compared to Th2 cells (referred to herein as Th1-associated miRs). In particular, the miR-17-92 gene cluster was found to exhibit significantly greater expression in Th1 cells. Over-expression of miR-17-92 in T cells promotes the Th1 phenotype. Thus, the use of Th1-associated miRs for cancer immunotherapy is described. Provided herein are isolated T cells containing a heterologous nucleic acid molecule encoding a Th1-associated miR, such as the miR17-92 gene cluster, or a portion thereof. Further provided is a method of treating cancer in a subject by administering to the subject an isolated T cell as disclosed herein. Also provided is a method of treating a subject with cancer by transfecting isolated T cells obtained from the subject with a heterologous nucleic acid molecule encoding a Th1-associated miR and administering the transfected T cells to the subject.

12 Claims, 11 Drawing Sheets

OTHER PUBLICATIONS

Papapetrou et al., "Harnessing endogenous miR-181a to segregate transgenic antigen receptor expression in developing versus posthymic T cells in murine hematopoietic chimeras," *The Journal of Clinical Investigation* 119: 157-168, 2009.

Rinaldi et al., "Concomitant *MYC* and microRNA Cluster miR-17-92 (*C13orf25*) Amplification in Human Mantle Cell Lymphoma," *Leuk Lymphoma*, 48:410-412, 2007.

Rodriguez et al., "Requirement of *bic/microRNA-155* for Normal Immune Function," *Science* 316:608-611, 2010.

Sasaki et al., "IL-4 Suppresses Very Late Antigen-4 Expression Which is Required for Therapeutic Th1 T Cell Trafficking into Tumors," *J Immunother*, 32:793-802, 2009.

Sasaki et al., "miR-17-92 expression in differentiated T cells—implications for cancer immunotherapy," *Journal of Translational Medicine* 8:17-28, 2010.

Sylvestre et al., "An E2F/miR-20a Autoregulatory Feedback Loop," *J Biol Chem*, 282:2135-2143, 2007.

Taguchi et al., "Identification of Hypoxia-Inducible Factor-1α as a Novel Target for *miR-17-92* MicroRNA Cluster," *Cancer Res*, 68:5540-5545, 2008.

Tanzer and Stadler, "Molecular Evolution of a MicroRNA Cluster," *J Mol Bio*, 339:327-335, 2004.

Thai et al., "Regulation of the Germinal Center Response by MicroRNA-155," *Science* 316:604-608, 2010.

Tili et al., "MicroRNAs, The Immune System and Rheumatic Disease," *Nat Clin Pract Rheum*, 4:534-541, 2008.

Ueda et al., "Dicer-regulated microRNAs 222 and 339 promote resistance of cancer cells to cytotoxic T-lymphocytes by down-regulation if ICAM-1," *Proc. Natl. Acad. Sci. USA* 106(26):10746-10751, 2009.

Uziel et al., "The *miR-17~92* Cluster Collaborates with the Sonic Hedgehog Pathway in Medulloblastoma," *Proc Natl Acad Sci U S A*, 106:2812-2817, 2009.

Ventura et al., "Targeted Deletion Reveals Essential and Overlapping Functions of the *miR-17 ~ 92* Family of miRNA Clusters," *Cell*, 132:875-886, 2008.

Volinia et al., "A microRNA Expression Signature of Human Solid Tumors Defines Cancer Gene Targets," *Proc Natl Acad Sci U S A*, 103:2257-2261, 2006.

Weber, "New Human and Mouse microRNA Genes Found by Homology Search," *FEBS J*, 272:59-73, 2005.

Woods et al., "Direct Regulation of an Oncogenic Micro-RNA Cluster by E2F Transcription Factors," *J Biol Chem*, 282:2130-2134, 2007.

Xiao and Rajewsky, "MicroRNA Control in the Immune System: Basic Principles," *Cell*, 136: 26-36, 2009.

Xiao et al., "Lymphoproliferative disease and autoimmunity in mice with elevated miR-17-92 expression in lymphocytes," *Nat Immunol.* 9(4): 405-414, 2008.

| NAME | Mouse Th1/Th2 |
|---|---|
| hsa-miR-142-3p | 3.86 |
| hsa-miR-92 | 3.66 |
| hsa-miR-20a | 3.66 |
| hsa-miR-106a | 3.642 |
| mmu-miR-106a | 3.561 |
| hsa-miR-30c | 3.551 |
| hsa-miR-19a | 3.492 |
| hsa-miR-20b | 3.451 |
| hsa-miR-142-3p | 3.355 |
| hsa-let-7g | 3.173 |
| hsa-miR-19b | 3.134 |
| hsa-miR-17-5p | 3.06 |
| hsa-miR-195 | 3.048 |
| mmu-miR-93 | 2.917 |
| hsa-miR-26a | 2.882 |
| hsa-miR-93 | 2.87 |
| hsa-miR-20b | 2.864 |
| hsa-let-7i | 2.704 |
| hsa-miR-21 | 2.566 |
| hsa-let-7f | 2.433 |
| hsa-let-7c | 2.408 |
| hsa-miR-106b | 2.369 |
| hsa-miR-98 | 2.35 |

TH1-ASSOCIATED MICRORNAS AND THEIR USE FOR TUMOR IMMUNOTHERAPY

CROSS REFERENCE TO RELATED APPLICATIONS

This application is a continuation of U.S. application Ser. No. 12/818,016, filed Jun. 17, 2010, which claims the benefit of U.S. Provisional Application No. 61/187,903, filed on Jun. 17, 2009. The above-listed applications are herein incorporated by reference in their entirety.

ACKNOWLEDGMENT OF GOVERNMENT SUPPORT

This invention was made with government support under grant number NS055140 awarded by the National Institutes of Health. The government has certain rights in the invention.

FIELD

This disclosure concerns microRNAs (miRs) that are differentially expressed in Th1 versus Th2 cells. This disclosure further relates to expression of such differentially expressed miRs in T cells as a means for tumor immunotherapy.

BACKGROUND

Preclinical studies involving immunotherapeutic strategies for central nervous system (CNS) tumors, such as glioblastoma multiforme (GBM), have demonstrated that tumor-specific T helper type-1 (Th1) and T cytotoxic type-1 (Tc1) cells, but not type-2 counterparts, can efficiently traffic into CNS tumor sites and mediate effective therapeutic efficacy, recruited via the type-1 chemokine CXCL10 (Nishimura et al., *Cancer Res* 2006, 66:4478-4487; Fujita et al., *J Immunol* 2008, 180:2089-2098; Fujita et al., *Cancer Res* 2009, 69:1587-1595) and the integrin receptor, very late antigen (VLA)-4 (Sasaki et al., *The Journal of Immunology* 2008, 181:104-108; Sasaki et al., *Eur J Immunol* 2008, 38:2865-2873; Zhu et al., *J Transl Med* 2007, 5:10; Sasaki et al., *Cancer Res* 2007, 67:6451-6458). Despite the importance of the type-1 T cell response, cancers, including GBMs, secrete numerous type-2 cytokines (Roussel et al., *Clin Exp Immunol* 1996, 105:344-352; Weller and Fontana, *Brain Res* 1995, 21:128-151; Nitta et al., *Brain Res* 1994, 649:122-128) that promote tumor proliferation (Jarnicki et al., *J Immunol* 2006, 177:896-904; Prokopchuk et al., *Br J Cancer* 2005, 92:921-928) and immune escape (Seo et al., *Immunology* 2001, 103:449-457). Hence, the strategic skewing of existing type-2 to type-1 immunity in glioma patients may be critical for the development of more effective immunotherapy.

MicroRNAs (miRs) are a novel class of endogenous small single-stranded RNA molecules which are 18-24 nucleotides in length (Hammond, *Cancer Chemother Pharmacol* 2006, 58 Suppl 1:s63-68). Mature miRs repress mRNA encoded protein translation and are highly conserved between species, including viruses, plants and animals (Elmen *Nature* 2008, 452:896-899). There are over 700 miRs identified in the human genome that collectively are predicted to regulate two-thirds of all mRNA transcripts (Hammond, *Cancer Chemother Pharmacol* 2006, 58 Suppl 1:s63-68). Findings over the past several years strongly support a role for miRs in the regulation of crucial biological processes, such as cellular proliferation (Cheng et al., *Nucleic Acids Res* 2005, 33:1290-1297), apoptosis (Xu et al., *Trends Genet.* 2004, 20:617-624), development (Karp and Ambros, *Science* 2005, 310:1288-1289), differentiation (Chen et al., *Science* 2004, 303:83-86), metabolism (Poy et al., *Nature* 2004, 432:226-230), and immune regulation (That et al., *Science* 2007, 316:604-608; O'Connell et al., *Proc Natl Acad Sci USA* 2007, 104:1604-1609). A recent study demonstrated that miR-222 and miR-339 in cancer cells down-regulate the expression of an intercellular cell adhesion molecule (ICAM)-1, thereby regulating the susceptibility of cancer cells to cytotoxic T lymphocytes (CTLs) (Ueda et al., *Proc Natl Acad Sci USA* 2009, 106: 10746-10751). This is among the first reports to demonstrate the role of miR in cancer immunosurveillance.

SUMMARY

Disclosed herein is the identification of miRNAs (miRs) that are up-regulated in Th1 cells compared to Th2 cells (referred to herein as Th1-associated miRs). Over-expression of Th1-associated miRs in T cells is demonstrated herein to promote the Th1 phenotype, which is critical for effective anti-tumor immune responses.

Thus, provided herein are isolated T cells containing a heterologous nucleic acid molecule encoding a Th1-associated miR. In some embodiments, the Th1-associated miR is the miR17-92 gene cluster, or a portion thereof. In some embodiments, the T cell is a tumor antigen-specific T cell. Further provided is a method of treating cancer in a subject by selecting a subject with cancer and administering to the subject an isolated T cell as disclosed herein.

Also provided is a method of treating a subject with cancer by (i) selecting a subject with cancer; (ii) isolating T cells from the subject; (iii) transfecting the isolated T cells with a heterologous nucleic acid molecule encoding a Th1-associated miR; and (iv) administering to the subject the isolated T cells transfected with the nucleic acid molecule encoding the Th1-associated miR. In some embodiments of the method, the heterologous nucleic acid molecule encodes the miR-17-92 transcript or a portion thereof. In some embodiments, the isolated T cell is a TA-specific T cell, such as a CTL.

The foregoing and other objects, features, and advantages of the invention will become more apparent from the following detailed description, which proceeds with reference to the accompanying figures.

SEQUENCE LISTING

Figure 1A:
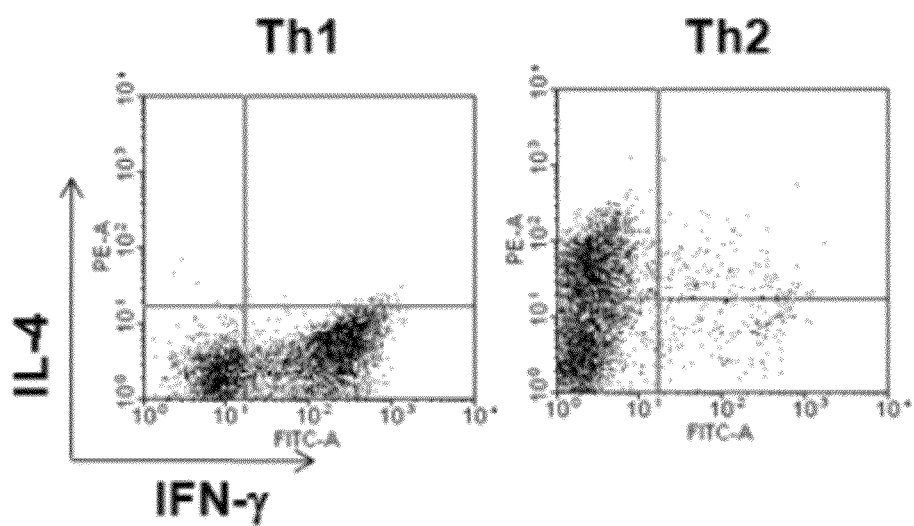
FIG. 1: Microarray analysis demonstrates up-regulation of miR-17-92 in Th1 cells. (A) Intracellular interferon (IFN)-γ vs. interleukin (IL)-4 expression of Th1 and T helper type-2 (Th2) cells induced from mouse CD4$^+$ splenic T cells in vitro. (B) Differentially expressed miRs were analyzed by hierarchical clustering of the log 2 value of Th1/Th2 pair of miR microarray signal. (C) miRs were ranked by relative fold expression in Th1/Th2 cells. Arrows indicate members of the miR-17-92 cluster or paralog clusters. miRs with a relative expression of >2.35-fold in Th1 are shown. (B and C) hsa- and mmu-indicate human and mouse miR probes, respectively. Hsa-probes can hybridize with most mouse miR due to the high homology and mmu-signals are shown only when murine miR has a unique sequence compared to its human counterpart. (D) Ideogram of mouse chromosome 14 showing the location and order of the miR-17-92 cluster (adapted from NCBI Blast).

The nucleic acid sequences listed in the accompanying sequence listing are shown using standard letter abbreviations for nucleotide bases, as defined in 37 C.F.R. 1.822. The Sequence Listing is submitted as an ASCII text file, created on Aug. 3, 2012, 4.99 KB, which is incorporated by reference herein. In the accompanying sequence listing:

SEQ ID NO: 1 is the nucleic acid sequence of the precursor form (stem-loop) of hsa-miR-17.

SEQ ID NO: 2 is the nucleic acid sequence of mature hsa-miR-17-5p.

SEQ ID NO: 3 is the nucleic acid sequence of mature hsa-miR-17-3p.

SEQ ID NO: 4 is the nucleic acid sequence of the precursor form (stem-loop) of mmu-miR-17.

SEQ ID NO: 5 is the nucleic acid sequence of mature mmu-miR-17-5p.

SEQ ID NO: 6 is the nucleic acid sequence of mature mmu-miR-17-3p.

SEQ ID NO: 7 is the nucleic acid sequence of the precursor form (stem-loop) of hsa-miR-18a.

SEQ ID NO: 8 is the nucleic acid sequence of mature hsa-miR-18a.

SEQ ID NO: 9 is the nucleic acid sequence of the precursor form (stem-loop) of mmu-miR-18a.

SEQ ID NO: 10 is the nucleic acid sequence of mature mmu-miR-18a.

SEQ ID NO: 11 is the nucleic acid sequence of the precursor form (stem-loop) of hsa-miR-19a.

SEQ ID NO: 12 is the nucleic acid sequence of mature hsa-miR-19a.

SEQ ID NO: 13 is the nucleic acid sequence of the precursor form (stem-loop) of mmu-miR-19a.

SEQ ID NO: 14 is the nucleic acid sequence of mature mmu-miR-19a.

SEQ ID NO: 15 is the nucleic acid sequence of the precursor form (stem-loop) of hsa-miR-20a.

SEQ ID NO: 16 is the nucleic acid sequence of mature hsa-miR-20a.

SEQ ID NO: 17 is the nucleic acid sequence of the precursor form (stem-loop) of mmu-miR-20a.

SEQ ID NO: 18 is the nucleic acid sequence of mature mmu-miR-20a.

SEQ ID NO: 19 is the nucleic acid sequence of the precursor form (stem-loop) of hsa-miR-19b-1.

SEQ ID NO: 20 is the nucleic acid sequence of mature hsa-miR-19b.

SEQ ID NO: 21 is the nucleic acid sequence of the precursor form (stem-loop) of mmu-miR-19b-1.

SEQ ID NO: 22 is the nucleic acid sequence of mature mmu-miR-19b.

SEQ ID NO: 23 is the nucleic acid sequence of the precursor form (stem-loop) of hsa-miR-92a-1.

SEQ ID NO: 24 is the nucleic acid sequence of mature hsa-miR-92a.

SEQ ID NO: 25 is the nucleic acid sequence of the precursor form (stem-loop) of mmu-miR-92a-1.

SEQ ID NO: 26 is the nucleic acid sequence of mature mmu-miR-92a.

DETAILED DESCRIPTION

I. Introduction

Type-1 T cells are critical for effective anti-tumor immune responses.

MicroRNAs (miRs) are a large family of small regulatory RNAs that control diverse aspects of cell function, including immune regulation. Disclosed herein is the identification of miRs differentially regulated between type-1 and type-2 T cells, and a determination of how the expression of such miRs is regulated.

MicroRNA microarray analyses was performed on in vitro differentiated murine T helper type-1 (Th1) and T helper type-2 (Th2) cells to identify differentially expressed miRs. Quantitative RT-PCR was used to confirm the differential expression levels. WST-1, ELISA and flow cytometry were also used to evaluate the survival, function and phenotype of cells, respectively. Mice transgenic for the identified miRs were employed to determine the biological impact of miR-17-92 expression in T cells.

The initial miR microarray analyses revealed that the miR-17-92 cluster is one of the most significantly over-expressed miRs in murine Th1 cells when compared with Th2 cells. RT-PCR confirmed that the miR-17-92 cluster expression was consistently higher in Th1 cells than Th2 cells. Disruption of IL-4 signaling through either IL-4 neutralizing antibody or knockout of STAT6 reversed the miR-17-92 cluster suppression in Th2 cells. Furthermore, T cells from tumor bearing mice and glioma patients had decreased levels of miR-17-92 when compared with cells from non-tumor bearing counterparts. CD4$^+$ T cells derived from miR-17-92 transgenic mice demonstrated superior type-1 phenotype with increased IFN-γ production and VLA-4 expression when compared with counterparts derived from wild type mice.

Human Jurkat T cells ectopically expressing increased levels of miR-17-92 cluster members demonstrated increased IL-2 production and resistance to AICD. Over-expression of miR-17-92 in primary T cells also renders these cells resistant to AICD. The inventors further demonstrate herein that miR-17-92 transgenic mice (which over-express miR-17-92 in T cells) exhibit significantly smaller tumors and/or greater length of survival following tumor challenge with either B16 melanoma cells or GL261 glioma cells.

The type-2-skewing tumor microenvironment induces the down-regulation of miR-17-92 expression in T cells, thereby diminishing the persistence of tumor-specific T cells and tumor control. Thus, genetic engineering of T cells to express miR-17-92 represents a promising approach for cancer immunotherapy.

II. Abbreviations

| | |
|---|---|
| AA | anaplastic astrocytomas |
| AICD | activation-induced cell death |
| APC | antigen presenting cell |
| BIL | brain infiltrating lymphocytes |
| CNS | central nervous system |
| CTL | cytotoxic T lymphocyte |
| ELISA | enzyme-linked immunosorbent assay |
| GBM | glioblastoma multiforme |
| GFP | green fluorescent protein |
| i.c. | intracranial |
| IFN | interferon |
| IL | interleukin |
| i.v. | intravenous |
| mAb | monoclonal antibody |
| MACS | magnetic activated cell separation |
| MHC | major histocompatibility complex |
| miR | microRNA |
| PBMC | peripheral blood mononuclear cells |
| PMA | phorbol 12-myristate 13-acetate |
| rh | recombinant human |
| rm | recombinant mouse |
| RNA | ribonucleic acid |
| RT-PCR | reverse transcriptase polymerase chain reaction |
| s.c. | subcutaneous |
| SPC | splenocyte |
| STAT | signal transducer and activator of transcription |
| TA | tumor antigen |
| Th1 | T helper type-1 |
| Th2 | T helper type-2 |
| Tc1 | T cytotoxic type-1 |
| Tc2 | T cytotoxic type-2 |
| TG | transgenic |
| VLA | very late antigen |
| WT | wild type |

II. Terms and Methods

Unless otherwise noted, technical terms are used according to conventional usage. Definitions of common terms in molecular biology may be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

In order to facilitate review of the various embodiments of the disclosure, the following explanations of specific terms are provided:

Administration: The introduction of a composition (such as a T cell) into a subject by a chosen route. For example, if the chosen route is intravenous, the composition is administered by introducing the composition into a vein of the subject.

Antigen: A compound, composition, or substance that can stimulate the production of antibodies or a T cell response in an animal, including compositions that are injected or absorbed into an animal. An antigen reacts with the products of specific humoral or cellular immunity, including those induced by heterologous immunogens. The term "antigen" includes all related antigenic epitopes. "Epitope" or "antigenic determinant" refers to a site on an antigen to which B and/or T cells respond.

Antigen-presenting cell (APC): A cell that can present antigen bound to MHC class I or class II molcules to T cells. APCs include, but are not limited to, monocytes, macrophages, dendritic cells, B cells, T cells and Langerhans cells. A T cell that can present antigen to other T cells (including CD4+ and/or CD8+ T cells) is an antigen presenting T cell (T-APC).

Chemotherapeutic agents: Any chemical agent with therapeutic usefulness in the treatment of diseases characterized by abnormal cell growth. Such diseases include tumors, neoplasms, and cancer as well as diseases characterized by hyperplastic growth such as psoriasis. In some cases, a chemotherapeutic agent is a radioactive compound. One of skill in the art can readily identify a chemotherapeutic agent of use (e.g., see Slapak and Kufe, *Principles of Cancer Therapy*, Chapter 86 in Harrison's Principles of Internal Medicine, 14th edition; Perry et al., *Chemotherapy*, Ch. 17 in Abeloff, Clinical Oncology $2^{nd}$ ed., © 2000 Churchill Livingstone, Inc; Baltzer, L., Berkery, R. (eds): Oncology Pocket Guide to Chemotherapy, 2nd ed. St. Louis, Mosby-Year Book, 1995; Fischer, D. S., Knobf, M. F., Durivage, H. J. (eds): The Cancer Chemotherapy Handbook, 4th ed. St. Louis, Mosby-Year Book, 1993). Combination chemotherapy is the administration of more than one agent to treat cancer.

Cytotoxic T lymphocyte (CTL): CTLs are a sub-group of T lymphocytes that are capable of inducing the death of infected cells or tumor cells, or cells that are otherwise damaged or dysfunctional. Most CTLs express CD8 and T-cell receptors (TCRs) that can recognize a specific antigenic peptide bound to Class I MHC molecules.

Glioma: A cancer of the brain that begins in glial cells (cells that surround and support nerve cells). Malignant gliomas are the most common type of primary brain tumor, and glioblastoma multiforme (GBM) is the most common and most malignant of the glial tumors. Other common malignant gliomas include anaplastic gliomas, including anaplastic astrocytomas.

Isolated: An "isolated" biological component (such as a nucleic acid molecule, protein, or cell) has been substantially separated or purified away from other biological components in the cell, blood or tissue of the organism, or the organism itself, in which the component naturally occurs, such as other chromosomal and extra-chromosomal DNA and RNA, proteins and cells. Nucleic acid molecules and proteins that have been "isolated" include those purified by standard purification methods. The term also embraces nucleic acid molecules and proteins prepared by recombinant expression in a host cell as well as chemically synthesized nucleic acid molecules and proteins.

Major histocompatibility complex (MHC): Generic designation meant to encompass the histocompatibility antigen systems described in different species, including the human leukocyte antigens ("HLA"). The term "motif" or "epitope" refers to the pattern of residues in a peptide of defined length, usually about 8 to about 11 amino acids, which is recognized by a particular MHC allele. The peptide motifs or epitopes are typically different for each MHC allele and differ in the pattern of the highly conserved residues and negative binding residues.

MicroRNA (miR): MicroRNAs (also known as miRNAs and miRs) are short RNA sequences expressed from longer transcripts found in the genomes of animals, plants and viruses and at least one single-celled eukaryote (Molnár et al., *Nature* 447:1126-1129, 2007; Zhao et al., *Genes Dev.* 21:1190-1203, 2007). MicroRNAs regulate the expression of target genes by binding to complementary sites in the target gene transcripts to cause translational repression or transcript degradation (Pillai et al., *Trends Cell Biol.* 17:118-126, 2007). These small RNA molecules have been implicated in a number of biological processes related to development, cell proliferation, apoptosis, metabolism, morphogenesis and disease (particularly cancer) (Kloosterman and Plasterk, *Dev. Cell* 11:441-450, 2006).

A gene encoding a microRNA is transcribed to form a primary transcript microRNA (pri-miRNA), which is processed to form a short stem-loop molecule, termed a precursor microRNA (pre-miRNA), followed by endonucleolytic cleavage to form the mature microRNA. Mature microRNAs are approximately 21-23 nucleotides in length and are partially complementary to the 3'UTR of one or more target messenger RNAs (mRNAs).

A nomenclature scheme has been well established for microRNAs (Griffiths-Jones et al., *Nucleic Acids Res.* 34:D140-D144, 2006; Ambros et al., *RNA* 9:277-279, 2003; Griffiths-Jones, *Nucleic Acids Res.* 32:D109-D111, 2004). For example, a microRNA name includes a three or four letter species prefix, such as "hsa" for *Homo sapiens*, and a numeric suffix, such as "150," resulting in a complete name of "hsa-miR-150." Mature miRNA sequences expressed from more than one hairpin precursor molecule are distinguished by "-1" and "-2" (such as miR-6-1 and miR-6-2). Related hairpin loci expressing related mature microRNA sequences have lettered suffixes (such as miR-181a and miR-181b). In some cases, mature miRNAs from both the 5' and 3' arms of the hairpin precursor are identified, which are designated "3p" or "5p" (such as miR-768-3p and miR-768-5p). Viral microRNA names relate to the locus from which the microRNA is derived (for example, ebv-miR-BART1 is from the Epstein-Barr virus BART locus).

MicroRNA gene product sequences are well described throughout the scientific and patent literature and are available online through miRBase (www.mirbase.org), provided by the University of Manchester (previously provided by the Sanger Institute). The miRBase registry provides the nucleotide sequences of all published animal, plant and viral microRNAs (Griffiths-Jones et al., *Nucleic Acids Res.* 36:D154-D158, 2008). Provided by miRBase are the sequences of precursor microRNAs (stem-loop miRNAs), mature miRNAs and minor microRNA species (miR*). Precursor miRNAs predominantly express one species of miRNA, referred to as the mature miRNA. However, minor miRNA sequences have also been detected and are referred to as miR*.

miR-17-92 gene cluster: Refers to the miR-17-92 transcript encoded by mouse chromosome 14 and human chromosome 13, or any homologous miR transcript in another species. The miR-17-92 transcript is the precursor for seven mature miRs: miR-17-5p, miR-17-3p, miR-18a, miR-19a, miR-20, miR-19b and miR-92. This miR cluster is homologous to the miR-106a cluster on the X chromosome and the miR-106-b-25 cluster on chromosome 5. In total, these three clusters contain 15 miR stem-loops, giving rise to 14 distinct mature miRs that fall into 5 miR families. Each member of these families has the identical seed region (the region of the miR that is important for binding to the 3'UTR of a target mRNA). As used herein, miR-17-92, miR-17-5p, miR-17-3p, miR-18a, miR-19a, miR-20, miR-19b and miR-92 refer to the respective miRs from any species that encodes these miRs. In some embodiments, the miR is a human miR. In other embodiments, the miR is a mouse miR. Exemplary miR sequences can be obtained from miRBase. In particular examples, the precursor and mature forms of human (hsa-) and mouse (mmu-) miR-17-5p, miR-17-3p, miR-18a, miR-19a, miR-20, miR-19b and miR-92 are set forth as SEQ ID NOs: 1-26, as listed below (miRBase accession numbers are listed next to the name of each miR):

hsa-mir-17 precursor, MI0000071
(SEQ ID NO: 1)
GUCAGAAUAAUGUCAAAGUGCUUACAGUGCAGGUAGUGAUAUGUGCAUC

UACUGCAGUGAAGGCACUUGUAGCAUUAUGGUGAC hsa-miR-17 (hsa-miR-17-5p), MIMAT0000070
(SEQ ID NO: 2)
CAAAGUGCUUACAGUGCAGGUAG hsa-miR-17* (hsa-miR-17-3p), MIMAT0000071
(SEQ ID NO: 3)
ACUGCAGUGAAGGCACUUGUAG mmu-mir-17 precursor, MI0000687
(SEQ ID NO: 4)
GUCAGAAUAAUGUCAAAGUGCUUACAGUGCAGGUAGUGAUGUGCAUC

UACUGCAGUGAGGGCACUUGUAGCAUUAUGCUGAC mmu-miR-17 (mmu-miR-17-5p), MIMAT0000649
(SEQ ID NO: 5)
CAAAGUGCUUACAGUGCAGGUAG mmu-miR-17* (mmu-miR-17-3p), MIMAT0000650
(SEQ ID NO: 6)
ACUGCAGUGAGGGCACUUGUAG hsa-mir-18a precursor, MI0000072
(SEQ ID NO: 7)
UGUUCUAAGGUGCAUCUAGUGCAGAUAGUGAAGUAGAUUAGCAUCUACU

GCCCUAAGUGCUCCUUCUGGCA hsa-miR-18a, MIMAT0000072
(SEQ ID NO: 8)
UAAGGUGCAUCUAGUGCAGAUAG mmu-mir-18a precursor, MI0000567
(SEQ ID NO: 9)
UGCGUGCUUUUUGUUCUAAGGUGCAUCUAGUGCAGAUAGUGAAGUAGAC

UAGCAUCUACUGCCCUAAGUGCUCCUUCUGGCAUAAGAAGUUAUGUC mmu-miR-18a, MIMAT0000528
(SEQ ID NO: 10)
UAAGGUGCAUCUAGUGCAGAUAG hsa-mir-19a precursor, MI0000073
(SEQ ID NO: 11)
GCAGUCCUCUGUUAGUUUUGCAUAGUUGCACUACAAGAAGAAUGUAGUU

GUGCAAAUCUAUGCAAAACUGAUGGUGGCCUGC hsa-miR-19a, MIMAT0000073
(SEQ ID NO: 12)
UGUGCAAAUCUAUGCAAAACUGA mmu-mir-19a precursor, MI0000688
(SEQ ID NO: 13)
GCAGCCCUCUGUUAGUUUUGCAUAGUUGCACUACAAGAAGAAUGUAGUU

GUGCAAAUCUAUGCAAAACUGAUGGUGGCCUGC mmu-miR-19a, MIMAT0000651
(SEQ ID NO: 14)
UGUGCAAAUCUAUGCAAAACUGA hsa-mir-20a precursor, MI0000076
(SEQ ID NO: 15)
GUAGCACUAAAGUGCUUAUAGUGCAGGUAGUGUUUAGUUAUCUACUGCA

UUAUGAGCACUUAAAGUACUGC hsa-miR-20a, MIMAT0000075
(SEQ ID NO: 16)
UAAAGUGCUUAUAGUGCAGGUAG mmu-mir-20a precursor, MI0000568
(SEQ ID NO: 17)
GUGUGAUGUGACAGCUUCUGUAGCACUAAAGUGCUUAUAGUGCAGGUAG

UGUGUAGCCAUCUACUGCAUUACGAGCACUUAAAGUACUGCCAGCUGUA

GAACUCCAG mmu-miR-20a, MIMAT0000529
(SEQ ID NO: 18)
UAAAGUGCUUAUAGUGCAGGUAG hsa-mir-19b-1 precursor, MI0000074
(SEQ ID NO: 19)
CACUGUUCUAUGGUUAGUUUUGCAGGUUUGCAUCCAGCUGUGUGAUAUU

CUGCUGUGCAAAUCCAUGCAAAACUGACUGUGGUAGUG hsa-miR-19b, MIMAT0000074
(SEQ ID NO: 20)
UGUGCAAAUCCAUGCAAAACUGA mmu-mir-19b-1 precursor, MI0000718
(SEQ ID NO: 21)
CACUGGUCUAUGGUUAGUUUUGCAGGUUUGCAUCCAGCUGUAUAAUAUU

CUGCUGUGCAAAUCCAUGCAAAACUGACUGUGGUGGUG mmu-miR-19b, MIMAT0000513
(SEQ ID NO: 22)
UGUGCAAAUCCAUGCAAAACUGA hsa-mir-92a-1 precursor, MI0000093
(SEQ ID NO: 23)
CUUUCUACACAGGUUGGGAUCGGUUGCAAUGCUGUGUUUCUGUAUGGUA

UUGCACUUGUCCCGGCCUGUUGAGUUUGG hsa-miR-92a, MIMAT0000092
(SEQ ID NO: 24)
UAUUGCACUUGUCCCGGCCUGU -continued mmu-mir-92a-1 precursor, MI0000719
(SEQ ID NO: 25)
CUUUCUACACAGGUUGGGAUUUGUCGCAAUGCUGUGUUUCUCUGUAUGG

UAUUGCACUUGUCCCGGCCUGUUGAGUUUGG mmu-miR-92a, MIMAT0000539
(SEQ ID NO: 26)
UAUUGCACUUGUCCCGGCCUG Open reading frame (ORF): A series of nucleotide triplets (codons) coding for amino acids without any internal termination codons. These sequences are usually translatable into a peptide.

Operably linked: A first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein-coding regions, in the same reading frame.

Patient: As used herein, the term "patient" includes human and non-human animals. The preferred patient for treatment is a human. "Patient" and "subject" are used interchangeably herein.

Pharmaceutically acceptable vehicles: The pharmaceutically acceptable carriers (vehicles) useful in this disclosure are conventional. *Remington's Pharmaceutical Sciences*, by E. W. Martin, Mack Publishing Co., Easton, Pa., 15th Edition (1975), describes compositions and formulations suitable for pharmaceutical delivery of one or more therapeutic compounds, molecules or agents.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (for example, powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Preventing, treating or ameliorating a disease: "Preventing" a disease refers to inhibiting the full development of a disease. "Treating" refers to a therapeutic intervention that ameliorates a sign or symptom of a disease or pathological condition after it has begun to develop. "Ameliorating" refers to the reduction in the number or severity of signs or symptoms of a disease.

Promoter: A promoter is an array of nucleic acid control sequences that directs transcription of a nucleic acid. A promoter includes necessary nucleic acid sequences near the start site of transcription, such as in the case of a polymerase II type promoter (a TATA element). A promoter also optionally includes distal enhancer or repressor elements which can be located as much as several thousand base pairs from the start site of transcription. Both constitutive and inducible promoters are included (see e.g., Bitter et al., *Methods in Enzymology* 153:516-544, 1987).

Sequence identity/similarity: The identity/similarity between two or more nucleic acid sequences, or two or more amino acid sequences, is expressed in terms of the identity or similarity between the sequences. Sequence identity can be measured in terms of percentage identity; the higher the percentage, the more identical the sequences are. Sequence similarity can be measured in terms of percentage similarity (which takes into account conservative amino acid substitutions); the higher the percentage, the more similar the sequences are. Homologs or orthologs of nucleic acid or amino acid sequences possess a relatively high degree of sequence identity/similarity when aligned using standard methods. This homology is more significant when the orthologous proteins or cDNAs are derived from species which are more closely related (such as human and mouse sequences), compared to species more distantly related (such as human and *C. elegans* sequences).

Methods of alignment of sequences for comparison are well known in the art. Various programs and alignment algorithms are described in: Smith & Waterman, *Adv. Appl. Math.* 2:482, 1981; Needleman & Wunsch, *J. Mol. Biol.* 48:443, 1970; Pearson & Lipman, *Proc. Natl. Acad. Sci. USA* 85:2444, 1988; Higgins & Sharp, *Gene*, 73:237-44, 1988; Higgins & Sharp, *CABIOS* 5:151-3, 1989; Corpet et al., *Nuc. Acids Res.* 16:10881-90, 1988; Huang et al. *Computer Appls. in the Biosciences* 8, 155-65, 1992; and Pearson et al., *Meth. Mol. Bio.* 24:307-31, 1994. Altschul et al., *J. Mol. Biol.* 215: 403-10, 1990, presents a detailed consideration of sequence alignment methods and homology calculations.

The NCBI Basic Local Alignment Search Tool (BLAST) (Altschul et al., *J. Mol. Biol.* 215:403-10, 1990) is available from several sources, including the National Center for Biological Information (NCBI) and on the internet, for use in connection with the sequence analysis programs blastp, blastn, blastx, tblastn and tblastx. Additional information can be found at the NCBI web site.

Subject: Living multi-cellular vertebrate organisms, a category that includes human and non-human mammals.

T Cell: A white blood cell critical to the immune response. T cells include, but are not limited to, $CD4^+$ T cells and $CD8^+$ T cells. A $CD4^+$ T lymphocyte is an immune cell that carries a marker on its surface known as "cluster of differentiation 4" (CD4). These cells, also known as helper T cells, help orchestrate the immune response, including antibody responses as well as killer T cell responses. $CD8^+$ T cells carry the "cluster of differentiation 8" (CD8) marker. In some embodiments, a CD8+ T cell is a cytotoxic T lymphocyte (CTL).

Th1-associated miR: Refers to any miR that is preferentially expressed in Th1 versus Th2 cells and/or promotes the Th1 phenotype when expressed (or over-expressed) in T cells. In some embodiments herein, the Th1-associated miR is the miR-17-92 gene cluster, or a portion thereof. In some embodiments, the Th1-associated miR is any one of the miR's listed in FIG. 1C. In other embodiments, the Th1-associated miR is miR-155 or miR-181a.

Therapeutically effective amount: A quantity of a specified composition, pharmaceutical or therapeutic agent sufficient to achieve a desired effect in a subject, or in a cell, being treated with the agent. The effective amount of the agent will be dependent on several factors, including, but not limited to the subject being treated, the disease or condition being treated, and the manner of administration of the therapeutic composition.

Transduce, Transform, or Transfect: To introduce a nucleic acid molecule into a cell, such as a vector encoding a miR. These terms encompass all techniques by which a nucleic acid molecule can be introduced into a cell, including but not limited to, transduction with viral vectors, transfection with plasmid vectors, and introduction of naked DNA by electroporation and particle gun acceleration. A transfected or transformed cell is a cell into which has been introduced a nucleic acid molecule by molecular biology techniques, such as a transformed T cell that includes a recombinant promoter operably linked to a reporter nucleic acid molecule. In some examples, the nucleic acid molecule becomes stably replicated by the cell, for example by incorporation of the nucleic acid molecule into the cellular genome, or by episomal replication. In other examples, the nucleic acid molecule is transiently expressed in the cell.

Tumor or cancer antigen: A cancer or tumor antigen is an antigen that can stimulate tumor-specific T-cell immune responses. Exemplary tumor antigens include, but are not limited to, RAGE-1, tyrosinase, MAGE-1, MAGE-2, NY-ESO-1, Melan-A/MART-1, glycoprotein (gp) 75, gp100, beta-catenin, PRAME, MUM-1, WT-1, CEA, and PR-1. Additional tumor antigens are known in the art (for example see Novellino et al., *Cancer Immunol. Immunother.* 54(3): 187-207, 2005) and are described below.

Tumor, cancer, neoplasia and malignancy: A neoplasm is an abnormal growth of tissue or cells that results from excessive cell division. Neoplastic growth can produce a tumor. The amount of a tumor in an individual is the "tumor burden" which can be measured as the number, volume, or weight of the tumor. A tumor that does not metastasize is referred to as "benign." A tumor that invades the surrounding tissue and/or can metastasize is referred to as "malignant." Malignant tumors are also referred to as "cancer."

Hematologic cancers are cancers of the blood or bone marrow. Examples of hematological (or hematogenous) cancers include leukemias, including acute leukemias (such as acute lymphocytic leukemia, acute myelocytic leukemia, acute myelogenous leukemia and myeloblastic, promyelocytic, myelomonocytic, monocytic and erythroleukemia), chronic leukemias (such as chronic myelocytic (granulocytic) leukemia, chronic myelogenous leukemia, and chronic lymphocytic leukemia), polycythemia vera, lymphoma, Hodgkin's disease, non-Hodgkin's lymphoma (indolent and high grade forms), multiple myeloma, Waldenstrom's macroglobulinemia, heavy chain disease, myelodysplastic syndrome, hairy cell leukemia and myelodysplasia. In some cases, lymphomas are considered solid tumors.

Solid tumors are abnormal masses of tissue that usually do not contain cysts or liquid areas. Solid tumors can be benign or malignant. Different types of solid tumors are named for the type of cells that form them (such as sarcomas, carcinomas, and lymphomas). Examples of solid tumors, such as sarcomas and carcinomas, include fibrosarcoma, myxosarcoma, liposarcoma, chondrosarcoma, osteosarcoma, and other sarcomas, synovioma, mesothelioma, Ewing's tumor, leiomyosarcoma, rhabdomyosarcoma, colon carcinoma, lymphoid malignancy, pancreatic cancer, breast cancer, lung cancers, ovarian cancer, prostate cancer, hepatocellular carcinoma, squamous cell carcinoma, basal cell carcinoma, adenocarcinoma, sweat gland carcinoma, medullary thyroid carcinoma, papillary thyroid carcinoma, pheochromocytomas sebaceous gland carcinoma, papillary carcinoma, papillary adenocarcinomas, medullary carcinoma, bronchogenic carcinoma, renal cell carcinoma, hepatoma, bile duct carcinoma, choriocarcinoma, Wilms' tumor, cervical cancer, testicular tumor, seminoma, bladder carcinoma, melanoma, and CNS tumors (such as a glioma (such as brainstem glioma and mixed gliomas), glioblastoma (also known as glioblastoma multiforme) astrocytoma, CNS lymphoma, germinoma, medulloblastoma, Schwannoma craniopharyogioma, ependymoma, pinealoma, hemangioblastoma, acoustic neuroma, oligodendroglioma, menangioma, neuroblastoma, retinoblastoma and brain metastasis).

Vector: A vector is a nucleic acid molecule allowing insertion of foreign nucleic acid without disrupting the ability of the vector to replicate and/or integrate in a host cell. A vector can include nucleic acid sequences that permit it to replicate in a host cell, such as an origin of replication. A vector can also include one or more selectable marker genes and other genetic elements. An expression vector is a vector that contains the necessary regulatory sequences to allow transcription and translation of inserted gene or genes. In some embodiments herein, the vector is a plasmid vector. In other embodiments, the vector is a viral vector. In some examples, the viral vector is a lentiviral vector.

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. Similarly, the word "or" is intended to include "and" unless the context clearly indicates otherwise. Hence "comprising A or B" means including A, or B, or A and B. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of the present disclosure, suitable methods and materials are described below. All publications, patent applications, patents, and other references mentioned herein are incorporated by reference in their entirety. In addition all GenBank accession numbers and miRBase accession numbers are herein incorporated by reference as they appear in the database on Jun. 17, 2010. In case of conflict, the present specification, including explanations of terms, will control. In addition, the materials, methods, and examples are illustrative only and not intended to be limiting.

III. Overview of Several Embodiments

Disclosed herein is the identification of miRs differentially regulated between type-1 and type-2 T cells. MicroRNA microarray analyses was performed on in vitro differentiated Th1 and Th2 cells to identify differentially expressed miRs. The miR microarray analyses identified the miR-17-92 cluster as one of the most significantly over-expressed miRs in Th1 cells when compared with Th2 cells. A number of additional miRs preferentially expressed in Th1 cells (referred to herein as "Th1-associated miRs") are listed in FIG. 1C.

It is demonstrated herein that T cells from tumor bearing mice and glioma patients have decreased levels of miR-17-92 when compared with cells from non-tumor bearing counterparts. CD4$^+$ T cells derived from miR-17-92 transgenic mice demonstrated superior type-1 phenotype with increased IFN-$\gamma$ production and VLA-4 expression when compared with counterparts derived from wild type mice. In addition, T cells ectopically expressing increased levels of miR-17-92 cluster members demonstrated increased IL-2 production and resistance to AICD. It is further demonstrated that miR-17-92 transgenic mice (which over-express miR-17-92 in T cells) exhibit significantly smaller tumors and/or greater length of survival following tumor challenge with either B16 melanoma cells or GL261 glioma cells. Thus, genetic engineering of T cells to express miR-17-92, or other Th1-associated miRs, is contemplated herein as new approach for cancer immunotherapy.

Provided is an isolated T cell comprising a heterologous nucleic acid molecule encoding at least one, at least two, at least three, at least four, at least five, at least six or at least seven Th1-associated miRs. In some embodiments, the heterologous nucleic acid molecule encodes the miR-17-92 transcript, or a portion thereof. In particular embodiments, the portion of the miR-17-92 transcript comprises the coding sequence for miR-17-5p, miR-17-3p, miR-18a, miR19a, miR-20a, miR19b-1 or miR-92a-1, or any combination of thereof. In specific examples, the portion comprises or consists of the coding sequence for (i) miR-17-5p, miR-17-3p, miR-18a and miR19a; (ii) miR-20a, miR19b-1 and miR-92a-1; or (iii) miR-17-5p and miR-17-3p.

In some embodiments, the Th1-associated miR is selected from miR-142-3p, miR-92, miR-20a, miR-106a, miR-30c, miR-19a, miR-20b, let-7g, miR-19b, miR-17-5p, miR-195, miR-93, miR-26a, miR-93, let-71, miR-21, let-7f, let-7c, miR-106b, miR-98, miR-155 and miR-181a.

In some embodiments, the heterologous nucleic acid molecule comprises a vector. The vector can be any vector suitable for transfection or transduction of T cells. Such vectors have been well described in the art and are well known to those of skill In some embodiments, the vector is a plasmid vector. In other embodiments, the vector is a viral vector. In some examples, the viral vector is a lentiviral vector.

In some embodiments, the isolated T cell is a tumor antigen (TA)-specific T cell, such as a cytotoxic T lymphocyte (CTL). Methods of isolating and/or producing TA-specific T cells are known in the art and are described in further detail in the sections below. Any method capable of isolating or generating sufficient numbers of TA-specific T cells for cancer immunotherapy is contemplated for use with the compositions and methods disclosed herein. In some embodiments, the T cell is engineered to express a molecule (such as a chimeric antigen receptor, antibody or fragment thereof) that specifically binds a tumor antigen. In some embodiments, the TA-specific T cell is generated by culturing the T cells ex vivo in the presence of antigen presenting cells expressing the tumor antigen. In other embodiments, the TA-specific T cells are TA-specific T cells isolated from a subject (such as tumor-infiltrating T cells).

In some embodiments, the TA is a glioma-associated antigen. However, any TA can be selected. The selection of TA is at least in part dependent on the type of cancer that is to be treated by administration of the TA-specific T cell expressing the Th1-associated miR.

Further provided are compositions comprising a pharmaceutically acceptable carrier and an isolated T cell transfected with a heterologous nucleic acid molecule encoding a Th1-associated miR, such as one or more of the miRs of the miR17-92 gene cluster. In some embodiments, the T cell is an TA-specific T cell, such as a TA-specific CTL.

Also provided is a method of treating a subject with cancer by (i) selecting a subject with cancer; and (ii) administering to the subject an isolated T cell transfected with a heterologous nucleic acid molecule encoding a Th1-associated miR, such as one or more of the miRs of the miR17-92 gene cluster, thereby treating the subject with cancer.

In some embodiments of the method, the isolated T cell comprises a heterologous nucleic acid molecule encoding a portion of the miR-17-92 transcript, wherein the portion of the miR-17-92 transcript comprises the coding sequence for miR-17-5p, miR-17-3p, miR-18a, miR19a, miR-20a, miR19b-1 or miR-92a-1, or any combination of 1, 2, 3, 4, 5, 6, or 7 miRs thereof. In specific examples, the portion comprises or consists of the coding sequence for (i) miR-17-5p, miR-17-3p, miR-18a and miR19a; (ii) miR-20a, miR19b-1 and miR-92a-1; or (iii) miR-17-5p and miR-17-3p. In some embodiments, the Th1-associated miR is selected from miR-142-3p, miR-92, miR-20a, miR-106a, miR-30c, miR-19a, miR-20b, let-7g, miR-19b, miR-17-5p, miR-195, miR-93, miR-26a, miR-93, let-71, miR-21, let-7f, let-7c, miR-106b, miR-98, miR-155 and miR-181a.

In some embodiments, the heterologous nucleic acid molecule comprises a vector, such as a plasmid vector, or a viral vector (for example, a lentiviral vector). In some embodiments, the T cell administered to the subject is a TA-specific CTL. The subject can have any type of cancer for which a TA is specifically expressed by the tumor cells (and is either not expressed by normal cells or is expressed at significantly reduced levels compared to tumor cells). In some embodiments, the subject has a glioma and the TA is a glioma-associated antigen.

Further provided is a method of treating a subject with cancer by (i) selecting a subject with cancer; (ii) isolating T cells from the subject; (iii) transfecting the isolated T cells with a heterologous nucleic acid molecule encoding at least one, at least two, at least three, at least four, at least five, at least six or at least seven Th1-associated miRs; and (iv) administering to the subject the isolated T cells transfected with the Th1-associated miR or miRs, thereby treating the subject with cancer. In some embodiments of the method, the Th1-associated miR is the miR-17-92 transcript, or a portion thereof. In some examples, the portion comprises the coding sequence for miR-17-5p, miR-17-3p, miR-18a, miR19a, miR-20a, miR19b-1 or miR-92a-1, or any combination of 1, 2, 3, 4, 5, 6 or 7 miRs thereof. In some embodiments, the Th1-associated miR is selected from miR-142-3p, miR-92, miR-20a, miR-106a, miR-30c, miR-19a, miR-20b, let-7g, miR-19b, miR-17-5p, miR-195, miR-93, miR-26a, miR-93, let-71, miR-21, let-7f, let-7c, miR-106b, miR-98, miR-155 and miR-181a. In some embodiments, the heterologous nucleic acid molecule comprises a vector, such as a plasmid vector, or a viral vector (for example, a lentiviral vector). In some embodiments, the T cell administered to the subject is a TA-specific CTL. The subject can have any type of cancer for which a TA is specifically expressed by the tumor cells (and is either not expressed by normal cells or is expressed at significantly reduced levels compared to tumor cells). In some embodiments, the subject has a glioma and the TA is a glioma-associated antigen.

In particular embodiments, the miR used is a miR from the species being treated. In some examples, the miR is a human miR, such as hsa-miR-17-5p, hsa-miR-17-3p, hsa-miR-18a, hsa-miR-19a, hsa-miR-20a, hsa-miR-19b, hsa-miR-92. In other examples, the miR is a mouse miR, such as mmu-miR-17-5p, mmu-miR-17-3p, mmu-miR-18a, mmu-miR-19a, mmu-miR-20a, mmu-miR-19b, mmu-miR-92. In particular examples, the human or mouse miRs comprise or consist of one of the sequences set forth in SEQ ID NO: 1 (precursor hsa-miR-17), SEQ ID NO: 2 (hsa-miR-17-5p), SEQ ID NO: 3 (hsa-miR-17-3p), SEQ ID NO: 4 (precursor mmu-miR-17), SEQ ID NO: 5 (mmu-miR-17-5p), SEQ ID NO: 6 (mmu-miR-17-3p), SEQ ID NO: 7 (precursor hsa-miR-18a), SEQ ID NO: 8 (hsa-miR-18a), SEQ ID NO: 9 (precursor mmu-miR-18a), SEQ ID NO: 10 (mmu-miR-18a), SEQ ID NO: 11 (precursor hsa-miR-19a), SEQ ID NO: 12 (hsa-miR-19a), SEQ ID NO: 13 (precursor mmu-miR-19a), SEQ ID NO: 14 (mmu-miR-19a), SEQ ID NO: 15 (precursor hsa-miR-20a), SEQ ID NO: 16 (hsa-miR-20a), SEQ ID NO: 17 (precursor mmu-miR-20a), SEQ ID NO: 18 (mmu-miR-20a), SEQ ID NO: 19 (precursor hsa-miR-19b-1), SEQ ID NO: 20 (hsa-miR-19b), SEQ ID NO: 21 (precursor mmu-miR-19b-1), SEQ ID NO: 22 (mmu-miR-19b), SEQ ID NO: 23 (precursor hsa-miR-92a-1), SEQ ID NO: 24 (hsa-miR-92a), SEQ ID NO: 25 (precursor mmu-miR-92a-1), SEQ ID NO: 26 (mmu-miR-92a). In some embodiments, the sequence of the human or mouse miR is at least 85%, at least 90%, at least 95%, or at least 99% identical to any one of the sequences set forth in SEQ ID NOs: 1-26.

In some embodiments of the treatment methods provided herein, the subject is further treated with a second (or additional) anti-cancer agent, such as a chemotherapeutic agent. In other embodiments, the subject is further treated with radiation therapy. In other embodiments, the subject is further treated by surgical removal of the tumor, or a portion thereof. Suitable combinations of treatments can be determined by a physician based on the type and severity of cancer and general health of the subject. Exemplary anti-cancer agents and treatment options are discussed in greater detail below.

IV. Use of miRs for Tumor Immunotherapy

A. Selection of miRs

The studies disclosed herein were driven by an effort to understand the potential roles of miRs in anti-tumor immunity. Thus, miRs differentially expressed in Th1 and Th2 cells were examined. FIG. 1C provides a list of miRs that exhibit a significant difference in expression between Th1 and Th2 cells.

i. miR17-92 Cluster

The miR microarray and RT-PCR analyses disclosed herein revealed that of all analyzed miRs, members of the miR-17-92 cluster (miR-17-92) are of the most significantly over-expressed miRs in Th1 cells when compared with Th2 cells. The miR-17-92 transcript encoded by mouse chromosome14 (and human chromosome 13) is the precursor for 7 mature miRs (miR-17-5p, miR-17-3p, miR-18a, miR-19a, miR-20a, miR-19b and miR-92) (Xiao et al., *Nat Immunol* 2008, 9:405-414; Xiao and Rajewsky, *Cell* 2009, 136:26-36). This cluster is also homologous to the miR-106a-363 cluster on the X chromosome and the miR-106b-25 cluster on chromosome 5. Together, these three clusters contain 15 miR stem-loops, giving rise to 14 distinct mature miRs that fall into 5 miR families. The members in each family have identical seed regions. This genomic organization is highly conserved in all vertebrates for which complete genome sequences are available (Tanzer and Stadler, *Journal of Molecular Biology* 2004, 339:327-335).

miRs in the miR-17-92 cluster are amplified in various tumor types, including B cell lymphoma and lung cancer, and promote proliferation and confer anti-apoptotic function in tumors, thereby promoting tumor-progression (He et al., Nature 2005, 435:828-833; Hayashita et al., *Cancer Res* 2005, 65:9628-9632; Matsubara et al., Oncogene 2007, 26:6099-6105; Lawrie, *Expert Opin Biol Ther* 2007, 7:1363-1374; Rinaldi et al., *Leuk Lymphoma* 2007, 48:410-412). Knockout and transgenic studies of the miR-17-92 cluster in mice have demonstrated the importance of this cluster in mammalian biology (Xiao and Rajewsky, *Cell* 2009, 136:26-36). Transgenic mice with miR-17-92 overexpressed in lymphocytes develop lymphoproliferative disorder and autoimmunity but not cancer (Xiao et al., *Nat Immunol* 2008, 9:405-414). These findings demonstrate a critical role for miR-17-92 cluster in T cell biology.

It is demonstrated herein that miR-17-92 is up-regulated in Th1 cells when compared with Th2 cells. IL-4 and STATE signaling mediate the down-regulation of miR-17-92. Tumor-bearing host conditions also suppress the miR-17-92 cluster expression in T cells, which is associated with a loss in ability to produce IFN-γ. This led to the hypothesis that miR-17-92 cluster overexpression would enhance type-1 responses. Indeed, it is demonstrated herein that type-1 T cells derived from miR-17-92 transgenic mice have a more pronounced type 1 phenotype including enhanced IFN-γ production and increased VLA-4 expression when compared with control type-1 T cells. These findings suggest that miR-17-92 plays a critical role in type-1 adaptive immunity. Accordingly, the use of miR-17-92 over-expression in T cells for cancer immunotherapy is disclosed herein.

ii. miR-155

Human mir-155 resides in the non-coding BIC transcript, located on chromosome 21 (Weber, *FEBS J.* 272:59-73, 2005). The mature form differs from that in mouse at a single position. miR-155 is processed from the BIC transcript in humans, and exhibits elevated expression in lymphoma samples (E is et al., *Proc Natl Acad Sci USA* 102:3627-3632, 2005). Previous studies have shown that miR-155 over-expression in hematopoietic cells induces malignancy (Costinean et al., *Proc Natl Acad Sci USA* 103:7024-7029, 2006) or myeloproliferative disorder in mice and is associated with human acute myeloid leukemia (O'Connell et al., *J Exp Med* 205:585-894, 2008). miR-155 also plays an important role in innate and adaptive immune responses (Tili et al., *Nat Clin Pract Rheum* 4:534-4541, 2008; Xiao and Rajewsky, *Cell* 136: 26-36, 2009). It has also been suggested that miR-155 is important for differentiation of Th1 and Th2 cells. Disruption of miR-155 in naïve T cells results in polarized differentiation preferentially into Th2 cells, with substantial production of Th2 cytokines (Rodriguez et al., *Science* 316: 608-611, 2007; That et al., *Science* 316:604-608, 2007). In addition, a recent study demonstrated that activation of T cells up-regulates miR-155 and over-expression of miR-155 in activated CD4+ T cells promotes Th1 differentiation through the regulation of IFN-γRα chain (Banerjee et al., *Eur J Immunol* 40:225-231, 2010; Okada et al., *Int J Biochem Cell Biol*, on-line publication Feb. 6, 2010). Thus, miR-155 is contemplated herein as a Th1-associated miR for use in cancer immunotherapy.

iii. miR-181a

Human miR-181a, cloned by Dostie et al. (*RNA* 9:180-186, 2003), is predicted to be expressed from two genomic hairpin loci, hsa-mir-181a-1 and hsa-mir-181a-2. A miRNA from the 3' arm of this hairpin, named miR-213, was predicted by computational methods using conservation with mouse and *Fugu rubripes* sequences, and validated in zebrafish (Lim et al., *Science* 299:1540, 2003). Subsequent cloning and Northern evidence shows that the 3' mature sequence is the biogenesis byproduct miR-181a*.

Previous studies have demonstrated that miR-181a augments the sensitivity of TCR-mediated T cell responses to peptide antigens. Regulation of T cell sensitivity by miR-181a enables mature T cells to abnormally recognize antagonists, the inhibitor peptide antisense, as agonists. In addition, miR-181a over-expression amplifies the strength and sensitivity of TCR-mediated activation (Li et al., *Cell* 129:147-161, 2007; Okada et al., *Int J Biochem Cell Biol*, on-line publication Feb. 6, 2010). Thus, miR-181a is contemplated herein as a Th1-associated miR for use in cancer immunotherapy.

iv. Other Differentially Expressed Th1-Associated miRs

Any miR that exhibits significantly greater expression in Th1 cells compared with Th2 cells is contemplated for use in the disclosed compositions and methods. FIG. 1C provides an exemplary list of such differentially expressed miRs. Th1-associated miRs include, but are not limited to, miR-142-3p, miR-92, miR-20a, miR-106a, miR-30c, miR-19a, miR-20b, let-7g, miR-19b, miR-17-5p, miR-195, miR-93, miR-26a, miR-93, let-71, miR-21, let-7f, let-7c, miR-106b and miR-98.

B. Tumor Immunotherapy

T cell immune responses are classified into distinct effector cell types based on their cytokine-secreting profiles. Type-2 T cells include Th2 and cytotoxic T 2 (Tc2), which preferentially secrete IL-4, IL-5, and IL-10, whereas type-1 T cells (Th1 and Tc1) predominantly secrete IFN-γ. The inventors' prior work has demonstrated that tumor-specific Th1 and Tc1, but not Th2 or Tc2, can efficiently traffic into CNS tumor sites and mediate effective therapeutic efficacy via the type-1 chemokine CXCL10 and an integrin receptor VLA-4. Despite the importance of the type-1 T cell response, cancers, including GBMs, secrete numerous type-2 and regulatory T cell (Treg)-inducing cytokines that promote tumor proliferation and immune escape. Thus, the strategic skewing of existing type-2/Treg to type-1 immunity in glioma patients (as well patients with other types of cancer) is critical for the development of more effective immunotherapy. In particular, the inventors propose it will be possible to generate genetically modified tumor-specific T cells ex vivo that are resistant to tumor-mediated immune suppression and possess robust anti-tumor type-1 functions. As disclosed herein, miR-17-92, when expressed in TA-specific T cells, has the potential to confer resistance to tumor-derived immunosuppressive factors and to improve type-1 reactivity in adoptively transferred T cells.

Although the effective expansion of tumor-reactive T cells by vaccination or in vitro expansion relies on the presence of sufficient TA-specific T cell precursors, the number and the avidity of self-reactive (i.e., TA-specific) T cells are typically low after the negative selection. Other barriers to develop effective immunotherapy for cancer include the poor persistence of TA-reactive T cells in cancer-bearing hosts. Thus, effective immunotherapy should employ strategies to improve the expansion of TA-specific T cells with the improved persistence and sensitivity to recognize TAs. As discussed herein, it is hypothesized that miR-17-92 has unique biological properties to overcome each of these challenges when effectively expressed in TA-specific T cells.

Any tumor type against which tumor antigen-specific CTLs are or can be generated is contemplated as a potential target of Th1-associated miR-transfected T cell immunotherapy. In some embodiments, the tumor is a CNS tumor. The CNS provides tumors an "immunologically privileged" status. A number of cellular and molecular mechanisms underlying the unique immuno-suppression of the CNS tumors have been delineated. These challenges underscore the need to develop new therapies to augment the host immune response to malignant gliomas. In the course of such work, however, it has become clear that this "privileged" status is not absolute. As demonstrated in cases of paraneoplastic cerebellar degeneration and experimental allergic encephalomyelitis, which resembles the pathology of multiple sclerosis, exposure of CNS-derived T cell antigens to the systemic immune system can induce specific T cell responses that recognize and attack immune targets located in the CNS. The presence of lymphocytes within the tumor can be a positive prognostic indicator of survival for patients with malignant gliomas. However, such naturally existing T cell response is not potent enough to mediate regression of gliomas.

Malignant gliomas are the most common type of primary brain tumor and a significant public health problem, with more than 12,000 new cases diagnosed each year in the United States. Glioblastoma multiforme (GBM) is by far the most common and most malignant of the glial tumors. Other common malignant gliomas include anaplastic gliomas, including anaplastic astrocytomas (AA). Patients with GBM or AA have a median survival of approximately 15 months, or 24 to 36 months, respectively. In addition, low-grade gliomas often progress to more malignant gliomas when they recur. No current treatment is curative because these tumors grow aggressively and invasively in the CNS. No significant advancements in the treatment of GBM have occurred in the past 25 years except for chemotherapy with temozolomide (TMZ) combined with radiotherapy, which demonstrated a limited prolongation of survival. The efficacy and safety of novel anti-angiogenic agents and a variety of targeted kinase inhibitors are controversial, and these concerns call for the strong need to develop novel efficacious and safe therapeutic modalities for these tumors.

Currently, a major challenge for immunotherapy of progressive malignant glioma is systemic suppression of immunity due to chemo-/radiotherapy, and tumor-elaboration of immunosuppressive substances, such as TGF-β and IL-10, which are known to suppress proliferation of T cells. While active immunization with glioma-associated antigen epitopes relies on intact host-immune reactivity, recent studies in melanoma patients demonstrated that passive immunization via intravenous adoptive transfer of tumor-reactive, ex vivo activated T cells may instead take advantage of conditions induced by preceding non-myeloablative but lympho-depleting chemotherapy regimens. This strategy may be particularly suitable for patients with malignant gliomas since the clinical use of chemotherapeutic agents is rapidly becoming a part of standard care in these patients.

Thus, the idea to generate genetically-modified tumor-specific T cells ex vivo, which are resistant to tumor-mediated immune suppression and possess the robust anti-tumor responses, as a means to elicit potent anti-tumor immune responses, is disclosed herein.

Although the treatment of glioma is exemplified herein, any type of cancer can be treated using the disclosed compositions and methods. Both hematological and solid cancers can be treated. Thus, in some embodiments, the hematological (or hematogenous) cancer is a leukemia, such as an acute leukemia (e.g., acute lymphocytic leukemia, acute myelocytic leukemia, acute myelogenous leukemia or myeloblastic, promyelocytic, myelomonocytic, monocytic or erythroleukemia), a chronic leukemia (such as chronic myelocytic (granulocytic) leukemia, chronic myelogenous leukemia, or chronic lymphocytic leukemia), polycythemia vera, lymphoma, Hodgkin's disease, non-Hodgkin's lymphoma (indolent or high grade forms), multiple myeloma, Waldenstrom's macroglobulinemia, heavy chain disease, myelodysplastic syndrome, hairy cell leukemia or myelodysplasia. In some cases, lymphomas are considered solid tumors.

In some embodiments, the cancer is a solid tumor. Solid tumors can be benign or malignant. Examples of solid tumors, such as sarcomas and carcinomas, include fibrosarcoma, myxosarcoma, liposarcoma, chondrosarcoma, osteosarcoma, and other sarcomas, synovioma, mesothelioma, Ewing's tumor, leiomyosarcoma, rhabdomyosarcoma, colon carcinoma, lymphoid malignancy, pancreatic cancer, breast cancer, lung cancers, ovarian cancer, prostate cancer, hepatocellular carcinoma, squamous cell carcinoma, basal cell carcinoma, adenocarcinoma, sweat gland carcinoma, medullary thyroid carcinoma, papillary thyroid carcinoma, pheochromocytomas sebaceous gland carcinoma, papillary carcinoma, papillary adenocarcinomas, medullary carcinoma, bronchogenic carcinoma, renal cell carcinoma, hepatoma, bile duct carcinoma, choriocarcinoma, Wilms' tumor, cervical cancer, testicular tumor, seminoma, bladder carcinoma, melanoma, and CNS tumors (such as a glioma (such as brainstem glioma and mixed gliomas), glioblastoma (also known as glioblastoma multiforme) astrocytoma, CNS lymphoma, germinoma, medulloblastoma, Schwannoma craniopharyogioma, ependymoma, pinealoma, hemangioblastoma, acoustic neuroma, oligodendroglioma, menangioma, neuroblastoma, retinoblastoma and brain metastasis).

V. Transduction of T Cells with Th1-Associated miRs and Adoptive Transfer Thereof Methods are disclosed herein for the treatment of a subject with cancer, such as a subject with a CNS tumor (for example, glioblastoma). The methods include the administration of a therapeutically effective amount of cytotoxic T lymphocytes (CTLs) over-expressing a Th1-associated miR (such as the miR-17-92 gene cluster or a portion thereof). In some embodiments, the CTLs are specific for an antigen of interest, such as a tumor antigen (TA-specific CTLs). By purifying and/or generating a purified population of selected TA-specific T cells from a subject ex vivo, transfecting the TA-specific CTLs with a heterologous nucleic acid encoding a Th1-associated miR (such as miR17-92) and introducing a therapeutic amount of these cells to the subject, the immune response of the recipient is enhanced, thereby treating the subject with cancer. In some embodiments of the methods disclosed herein, the isolated T cells transfected with a Th1-associated miR were isolated from the subject to be treated (autologous T cells). In some examples, the autologous T cells are TA-specific CTLs. For example, TA-specific T cells can be isolated from the tumor of a subject (referred to as tumor-infiltrating T lymphocytes). In other examples, T cells can be isolated from a subject (such as from the blood) and subjected to particular ex vivo culture conditions to produce a population of TA-specific CTLs. In yet other examples, T cells can be isolated from the subject to be treated and then engineered to express chimeric antigen receptors that specifically bind a tumor antigen.

Methods of isolating T cells are routine in the art. For example, blood cells (such as PBMCs) can be obtained from the subject, such as by using leukapheresis. If desired, non-T cell subpopulations (such as dendritic cells) can be depleted from the PBMCs prior to introducing nucleic acid molecules encoding a selected miR, such as miR-17-92. The isolated cells can be cryopreserved until needed.

In some embodiments, the T cells isolated from a subject are engineered to express a chimeric antigen receptor. Methods of engineering T cells to express chimeric antigen receptors have been described and are well known to those of skill in the art (see, for example, PCT Publication Nos. WO 2005/02383; WO 2006/060878; WO2010/025177 and WO 2009/126789; and U.S. Pat. No. 6,410,319, each of which is herein incorporated by reference). The engineered T cells are further transfected with a vector encoding a Th1-associated miR (such as the miR-17-92 gene cluster, or a portion thereof). A therapeutically effective amount of the antigen-specific engineered T cells transfected with the Th1-associated miR is administered to the recipient, thereby producing an immune response to the antigen of interest in the recipient.

In one example disclosed herein, the method includes isolating T cells from the subject to be treated and contacting the isolated T cells with a population of antigen presenting cells (APCs) from the subject that are presenting an antigen of interest, thereby producing a population of isolated T cells that recognize an antigen of interest. The population of activated T cells is transfected with a vector encoding a Th1-associated miR (such as the miR-17-92 gene cluster, or a portion thereof). A therapeutically effective amount of the TA-specific T cells transfected with the Th1-associated miR is administered to the subject, producing an immune response to the antigen of interest in the subject, thereby treating the subject with cancer.

To increase the number of antigen-specific T cells, proliferation of the cells can be stimulated, for example by incubation in the presence of a cytokine, such as IL-2, IL-7, IL-12 and IL-15. The amount of cytokine added is sufficient to stimulate production and proliferation of T cells, and can be determined using routine methods. In some examples, the amount of IL-2, IL-7, IL-12, or IL-15 added is about 0.1-100 IU/mL, such as at least 1 IU/mL, at least 10 IU/mL, or at least 20 IU/mL.

Tumor antigens are proteins that are produced by tumor cells that elicit an immune response, particularly T-cell mediated immune responses. The isolated T cells can be specific for any tumor antigen. The selection of tumor antigen will depend on the particular type of cancer to be treated. Tumor antigens are well known in the art and include, for example, a glioma-associated antigen, carcinoembryonic antigen (CEA), β-human chorionic gonadotropin, alphafetoprotein (AFP), lectin-reactive AFP, thyroglobulin, RAGE-1, MN-CA IX, human telomerase reverse transcriptase, RU1, RU2 (AS), intestinal carboxyl esterase, mut hsp70-2, M-CSF, prostase, prostate-specific antigen (PSA), PAP, NY-ESO-1, LAGE-1a, p53, prostein, PSMA, Her2/neu, survivin and telomerase, prostate-carcinoma tumor antigen-1 (PCTA-1), MAGE, ELF2M, neutrophil elastase, ephrinB2, CD22, insulin growth factor (IGF)-I, IGF-II, IGF-I receptor and mesothelin. A list of exemplary tumor antigens and their associated tumors are shown below in Table 1.

TABLE 1

Exemplary tumors and their tumor antigens

| Tumor | Tumor Associated Target Antigens |
|---|---|
| Acute myelogenous leukemia | Wilms tumor 1 (WT1), preferentially expressed antigen of melanoma (PRAME), PR1, proteinase 3, elastase, cathepsin G |
| Chronic myelogenous leukemia | WT1, PRAME, PR1, proteinase 3, elastase, cathepsin G |
| Myelodysplastic syndrome | WT1, PRAME, PR1, proteinase 3, elastase, cathepsin G |
| Acute lymphoblastic leukemia | PRAME |
| Chronic lymphocytic leukemia | Survivin |
| Non-Hodgkin's lymphoma | Survivin |
| Multiple myeloma | NY-ESO-1 |
| Malignant melanoma | MAGE, MART, Tyrosinase, PRAME GP100 |
| Breast cancer | WT1, herceptin, epithelial tumor antigen (ETA) |
| Lung cancer | WT1 |
| Ovarian cancer | CA-125 |
| Prostate cancer | PSA |
| Pancreatic cancer | CA19-9, RCAS1 |
| Colon cancer | CEA |
| Renal cell carcinoma (RCC) | Fibroblast growth factor 5 |
| Germ cell tumors | AFP |

A nucleic acid encoding the selected Th1-associated miR (such as a plasmid vector or viral vector encoding the miR) can be introduced into the isolated T cells, thus resulting in transformed T cells. Methods for transduction of such vectors into T cells are routine in the art.

In some embodiments, the nucleic acid molecule encoding the Th1-associated miR is a vector encoding the selected miR. A number of different plasmid and viral vectors have been described and are well known in the art. In some embodiments of the methods, the vector is a non-viral vector (for example, a plasmid). In other embodiments, the vector is a viral vector (for example, an adenoviral, adeno-associated viral, retroviral or lentiviral vector). Suitable vectors are well known in the art.

Retrovirus, including lentivirus, vectors can also be used with the methods described herein. Lentiviruses include, but are not limited to, human immunodeficiency virus (such as HIV-1 and HIV-2), feline immunodeficiency virus, equine infectious anemia virus and simian immunodeficiency virus. Other retroviruses include, but are not limited to, human T-lymphotropic virus, simian T-lymphotropic virus, murine leukemia virus, bovine leukemia virus and feline leukemia virus. Methods of generating retrovirus and lentivirus vectors and their uses have been well described in the art (see, for example, U.S. Pat. Nos. 7,211,247; 6,979,568; 7,198,784; 6,783,977; and 4,980,289, each of which is herein incorporated by reference).

In addition, adenovirus vectors can be first, second, third and/or fourth generation adenoviral vectors or gutless adenoviral vectors. Adenovirus vectors can be generated to very high titers of infectious particles; infect a great variety of cells; efficiently transfer genes to cells that are not dividing; and are seldom integrated in the host genome, which avoids the risk of cellular transformation by insertional mutagenesis (Douglas and Curiel, *Science and Medicine*, March/April 1997, pages 44-53; Zern and Kresinam, *Hepatology* 25(2), 484-491, 1997). Representative adenoviral vectors are described by Stratford-Perricaudet et al. (*J. Clin. Invest.* 90: 626-630, 1992); Graham and Prevec (In Methods in Molecular Biology: Gene Transfer and Expression Protocols 7: 109-128, 1991); and Barr et al. (*Gene Therapy*, 2:151-155, 1995), which are herein incorporated by reference.

Adeno-associated virus (AAV) vectors can also be used. Methods of generating AAV vectors, administration of AAV vectors and their use are well known in the art (see, for example, U.S. Pat. No. 6,951,753; U.S. Patent Application Publication Nos. 2007-036757, 2006-205079, 2005-163756, 2005-002908; and PCT Publication Nos. WO 2005/116224 and WO 2006/119458).

Administration of a therapeutic amount of tumor antigen-specific T cells over-expressing a Th1-associated miR can be used to treat a primary tumor, to prevent recurrence of the tumor in the subject, or to treat a relapse of the tumor.

A therapeutically effective amount of TA-specific T cells engineered to express a Th1-associated miR is administered to the subject. Specific, non-limiting examples of a therapeutically effective amount of isolated T cells include cells administered at a dose of about $1\times10^5$ cells per kilogram of subject to about $1\times10^9$ cells per kilogram of subject, such as from about $1\times10^6$ cells per kilogram to about $1\times10^8$ cells per kilogram, such as from about $5\times10^6$ cells per kilogram to about $7.5\times10^7$ cells per kilogram, such as at about $2.5\times10^7$ cells per kilogram, or at about $5\times10^7$ cells per kilogram.

Isolated TA-specific T cells engineered to express a Th1-associated miR can be administered in single or multiple doses as determined by a clinician. For example, the cells can be administered at intervals of approximately one week, two weeks, four weeks, one month or two months depending on the response desired and the response obtained. In some examples, once the desired response is obtained, no further TA-specific T cells are administered. However, if the recipient displays one or more symptoms associated with the presence or growth of a tumor, a therapeutically effective amount of TA-specific T cells can be administered at that time. The administration can be local or systemic.

The purified antigen-specific T cells disclosed herein can be administered with a pharmaceutically acceptable carrier, such as saline. Other therapeutic agents can be administered before, during, or after administration of the TA-specific T cells engineered to express a Th1-associated miR, depending on the desired effect (as discussed in greater detail below).

VI. Combination Treatment Methods

Th1-associated miR-transfected T cell immunotherapy can be used alone or can be accompanied by administration of other anti-cancer agents or therapeutic treatments (such as surgical resection of a tumor or radiation therapy). Any suitable anti-cancer agent can be administered to a patient as part of a treatment regimen that includes T cell immunotherapy. Exemplary anti-cancer agents include, but are not limited to, chemotherapeutic agents, such as, for example, mitotic inhibitors, alkylating agents, anti-metabolites, intercalating antibiotics, growth factor inhibitors, cell cycle inhibitors, enzymes, topoisomerase inhibitors, anti-survival agents, biological response modifiers, anti-hormones (e.g. anti-androgens) and anti-angiogenesis agents. Other anti-cancer treatments include radiation therapy and antibodies that specifically target cancer cells.

Examples of alkylating agents include nitrogen mustards (such as mechlorethamine, cyclophosphamide, melphalan, uracil mustard or chlorambucil), alkyl sulfonates (such as busulfan), nitrosoureas (such as carmustine, lomustine, semustine, streptozocin, or dacarbazine).

Examples of antimetabolites include folic acid analogs (such as methotrexate), pyrimidine analogs (such as 5-FU or cytarabine), and purine analogs, such as mercaptopurine or thioguanine.

Examples of natural products include vinca alkaloids (such as vinblastine, vincristine, or vindesine), epipodophyllotoxins (such as etoposide or teniposide), antibiotics (such as dactinomycin, daunorubicin, doxorubicin, bleomycin, plicamycin, or mitocycin C), and enzymes (such as L-asparaginase).

Examples of miscellaneous agents include platinum coordination complexes (such as cis-diamine-dichloroplatinum II also known as cisplatin), substituted ureas (such as hydroxyurea), methyl hydrazine derivatives (such as procarbazine), and adrenocrotical suppressants (such as mitotane and aminoglutethimide).

Examples of hormones and antagonists include adrenocorticosteroids (such as prednisone), progestins (such as hydroxyprogesterone caproate, medroxyprogesterone acetate, and magestrol acetate), estrogens (such as diethylstilbestrol and ethinyl estradiol), antiestrogens (such as tamoxifen), and androgens (such as testerone proprionate and fluoxymesterone).

Examples of many of the most commonly used chemotherapy drugs include Adriamycin, Alkeran, Ara-C, BiCNU, Busulfan, CCNU, Carboplatinum, Cisplatinum, Cytoxan, Daunorubicin, DTIC, 5-FU, Fludarabine, Hydrea, Idarubicin, Ifosfamide, Methotrexate, Mithramycin, Mitomycin, Mitoxantrone, Nitrogen Mustard, Taxol (or other taxanes, such as docetaxel), Velban, Vincristine, VP-16, while some more newer drugs include Gemcitabine (Gemzar), Herceptin, Irinotecan (Camptosar, CPT-11), Leustatin, Navelbine, Rituxan STI-571, Taxotere, Topotecan (Hycamtin), Xeloda (Capecitabine), Zevelin and calcitriol.

Non-limiting examples of immunomodulators that can be used include AS-101 (Wyeth-Ayerst Labs.), bropirimine (Upjohn), gamma interferon (Genentech), GM-CSF (granulocyte macrophage colony stimulating factor; Genetics Institute), IL-2 (Cetus or Hoffman-LaRoche), human immune globulin (Cutter Biological), IMREG (from Imreg of New Orleans, La.), SK&F 106528, and TNF (tumor necrosis factor; Genentech).

Another treatment for cancer is surgical treatment, for example surgical resection of the tumor or a portion of it. Another example of a treatment is radiotherapy, for example administration of radioactive material or energy (such as external beam therapy) to the tumor site to help eradicate the tumor or shrink it prior to surgical resection.

When used in combination with T cell immunotherapy, the additional treatment methods described above can be administered or performed prior to, at the same time, or following T cell immunotherapy as appropriate for the particular patient, the cancer to be treated and the specific combination of therapies.

The following examples are provided to illustrate certain particular features and/or embodiments. These examples should not be construed to limit the disclosure to the particular features or embodiments described.

EXAMPLES

Example 1

Materials and Methods

This example describes the experimental procedures used for the studies described in Example 2.
Reagents RPMI 1640, FBS, L-glutamine, sodium pyruvate, 2-mercaptoethanol, nonessential amino acids, and penicillin/streptomycin were obtained from Invitrogen Life Technologies. Recombinant murine (rm) IL-12 was purchased from Cell Sciences Technologies. RmIL-4, recombinant human (rh) IL-4 and rhIL-2 were purchased from PeproTech. Purified mAbs against IL-12 (C15.6), IFN-γ (R4-6A2), IL-4 (11B11), CD3 (145-2C11), CD4 (RM4-5), CD8 (53-6.7) and CD49d (R1-2) were all purchased from BD Pharmingen. Purified mAbs against CD3 (UCHT1), CD28 (CD28.2) and IL-4 (MP4-25D2) were purchased from Biolegend. RT-PCR reagents and primers were purchased from Applied Biosystems and analyzed on a BioRad IQ5. WST-1 reagent was purchased from Roche. For isolation of T cells, immunomagnetic isolation kits from Miltenyi Biotec were used. All reagents and vectors for lentiviral production were purchased from System Biosciences with the exception of LIPOFECTAMINE™ 2000, which was from Invitrogen.
Mice C57BL/6 mice and C57BL/6 background STATE deficient mice (B6.12952[C]-State$^{tm1Gru}$/J), both 5-9 weeks of age, were purchased from The Jackson Laboratory. C57BL/6-background miR-17-92 transgenic (TG) mice (C57BL/6-Gt [ROSA]26Sor$^{tm3(CAG-MIRN17-92,-EGFP)Rsky}$/J; The Jackson Laboratory) were maintained as breeding colonies and bred to C57BL/6-background mice transgenic for Cre recombinase gene under the control of the Lck promoter (B6.Cg-Tg [Lck-cre]548Jxm/J, the Jackson Laboratory) to obtain mice in which T cells expressed miR-17-92 at high levels (miR-17-92 TG/TG). For mouse tumor experiments, C57BL/6 mice and C57BL/6 background STAT6$^{-/-}$ mice received subcutaneous injection of $1 \times 10^6$ B 16 tumor cells resuspended in PBS into the right flank. On day 15 following tumor inoculation, mice were sacrificed and splenic T cells were isolated.
T cells from Healthy Donors and Patients with GBM To determine the impact of IL-4, healthy donor-derived CD4$^+$ T cells were isolated with immunomagnetic separation and stimulated with 100 IU/ml rhIL-2, anti-CD3 and anti-CD28 mAbs (1 µg/ml for each) in the presence or absence of rhIL-4(10 ng/ml). RT-PCR analyses were performed with both healthy donor- and patient-derived T cells to determine the expression of miR-17-92 as described in the relevant section.

Th1 and Th2 Cell Culture

Th1 and Th2 cells were differentiated from immunomagnetically-separated CD4$^+$ splenic T cells. Magnetic activated cell separation (MACS) was carried out using positive selection. Briefly, spleens were minced in complete media, resuspended in red blood cell lysis buffer and stained with immunomagnetically labeled anti-CD4 antibody. Cells were then washed and placed through the magnetic column in 500 µl of MACS buffer. The column was then washed 3 times with buffer and then removed from the magnet and labeled cells were extracted in 3 ml of MACS buffer.

For differentiation of T cells, purified CD4$^+$ cells were stimulated in 48-well plates with anti-CD3 mAb (5 µg/ml) in the presence of irradiated C57BL/6 spleen cells (3000 Rad) as feeder cells. RmIL-12 (4 ng/ml), rmIFN-γ (4 ng/ml), anti-IL-4 mAb (10 µg/ml) and rhIL-2 (100 IU/ml) were added for Th1 development. Th2 cells were generated from the same CD4$^+$ cell precursors stimulated with anti-CD3 mAb and feeder cells in the presence of rmIL-4 (50 ng/ml), two anti-IFN-γ mAbs (10 µg/ml), anti-IL-12 mAb (10 µg/ml) and rhIL-2 (100 IU/mL). After 10 days, cells were stained for IL-4 and IFN-γ to confirm differentiation. Neutral cell culture included anti-CD3, feeder cells and rhIL-2. For studies involving IL-4 blockade, 12.5 ng/ml anti-human IL-4 mAb (Biolegend) was used in human experiments and 2.5 µg/ml anti-mouse IL-4 mAb (11B11) in murine studies. IFN-γ and IL-4 in the culture supernatants were measured using specific ELISA kits (R&D Systems). For FACs analysis, cells were incubated with mAb at 4° C. for 30 minutes, washed twice in staining buffer, and fixed in 500 µl of 2% paraformaldehyde in PBS. Cells were stored in the dark at 4° C. until analysis. Flow cytometry was carried out on the Coulter XL four-color flow cytometer.
miR Microarray Total RNA was isolated from Th1 and Th2 cells using the TRIZOL™ reagent and quality was confirmed with an A260/A280 ratio greater than 1.85. Two 1 µg of total RNA was labeled with either Hy5 (red; Th1) or Hy3 (green; Th2) fluorescent dyes using miRCURY™ LNA microRNA labeling kit (Exiqon, Woburn, Mass.) according to the manufacturer's protocol. Labeled miR samples in duplicate were co-hybridized on miR array slides, a custom spotted miR array V4P4 containing duplicated 713 human, mammalian and viral mature antisense microRNA species (miRBase, version 9.1) plus 2 internal controls with 7 serial dilutions printed in house (Immunogenetics Laboratory, Department of Transfusion Medicine, Clinical Center, National Institutes of Health) (Ren et al., *Journal of Translational Medicine* 2009, 7:20). After washing, raw intensity data were obtained by scanning the chips with GENEPIX™ scanner Pro 4.0 and were normalized by median over entire array. Differentially expressed miRs were defined by mean (n=2) fold change (Th1/Th2 signal intensity)>2.
Quantitative RT-PCR Total RNA was extracted using the Qiagen RNEASY™ kit and quality was confirmed with a A260/A280 ration greater than 1.85. RNA was subjected to RT-PCR analysis using the TAQMAN™ microRNA Reverse Transcription Kit, microRNA Assays (Applied Biosystems), and the Real-Time thermocycler iQ5 (Bio-Rad). The small nucleolar SNO202 was used as the housekeeping small RNA reference gene for all murine samples and RNU43 for human samples. All reactions were done in triplicate and relative expression of RNAs was calculated using the $\Delta\Delta C_T$ method (Livak and Schmittgen, *Methods* 2001, 25:402-408).

WST-1 Proliferation Assay

For WST-1 proliferation assays, $1 \times 10^4$ cells were cultured in a 96-well plate for 24-48 hours in 100 μl of complete media. Then, 10 μl of WST-1 reagent was added to each well. Cells were incubated at 37° C., 5% $CO_2$ for 4 hours, and placed on a shaker for 1 minute. The plates were then read on a micro plate reader with a wavelength of 420 nm and a reference at 620 nm.

Assays using Jurkat Lymphoma Cells Transduced with miR-17-92

Jurkat human T cell leukemia cells (American Type Culture Collection) were transduced by either one of the following pseudotyped lentiviral vectors: 1) control vector encoding GFP; 2) the 17-92-1 expression vector encoding miR-17, miR-18 and miR-19; or 3) the 17-92-2 expression vector encoding miR-20, miR-19b-1, and miR-92a-1. All vectors were purchased from SBI. Lentiviral particles were produced by co-transfecting confluent 293TN cells (SBI) with pPACK-H1 Lentivirus Packaging Kit (SBI) and the miR containing expression vectors (SBI) noted above using LIPO-FECTAMINE™ 2000 reagent (Invitrogen). Supernatant was collected after 48 hour incubation at 37° C. with 5% $CO_2$ and placed at 4° C. with PEG-it Virus Concentration Solution (SBI) for 24 hrs. Supernatants/PEG solutions were then centrifuged and the pellet was resuspended in a reduced volume of media as viral stock. Jurkat cells were further resuspended in the viral stock together with polybrene (8 μg/ml) for 24 hours. Fresh media was then added to the cells and transduction efficiency was evaluated by GFP expressing cells. For IL-2 production, transduced Jurkat cells were stimulated with phorbol 12-myristate 13-acetate (PMA; 10 ng/ml) and ionomycin (500 nM) overnight and supernatant was assayed for IL-2 by a human IL-2 ELISA kit. For AICD, cells were treated with 10 μg/ml purified anti-CD3 mAb (UCHT1) from Biolegend for 24 hours and then cell viability was measured using WST-1 reagent.

Statistical Methods

All statistical analyses were carried out on Graphpad Prism software. The statistical significance of differences between groups was determined using student t-test. Differences were considered significant when $p<0.05$. A post test for linear trend was used to determine linear trend and $p<0.05$ was considered to be significant.

Example 2 miR-17-92 Expression in Differentiated T Cells

Figure 1D:
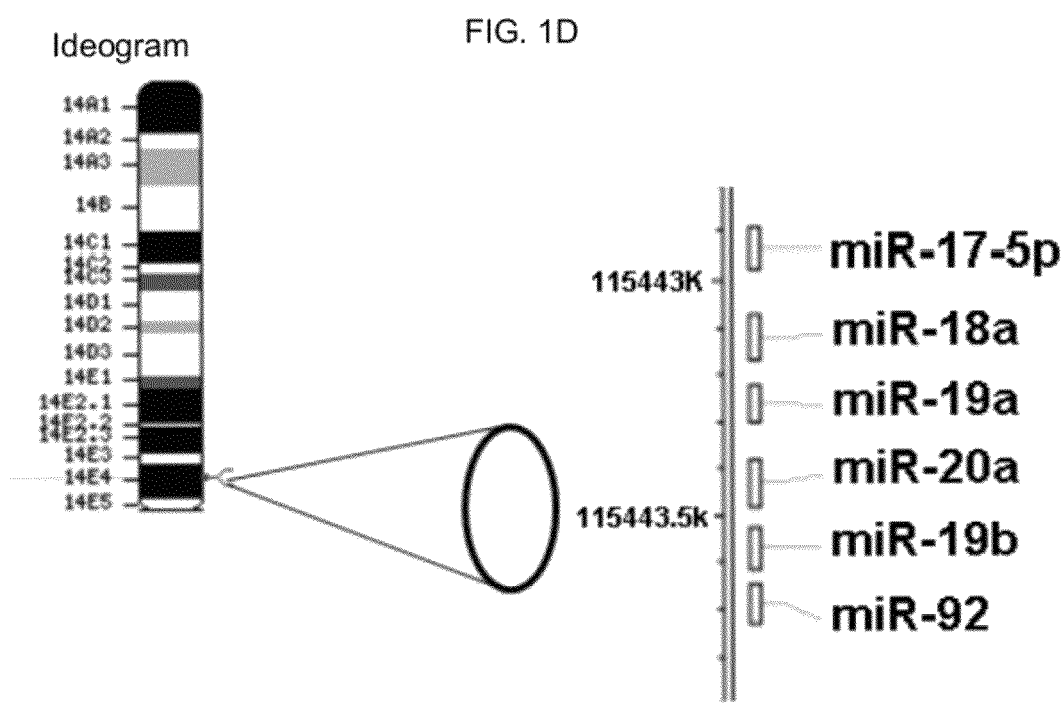
Figure 2A:
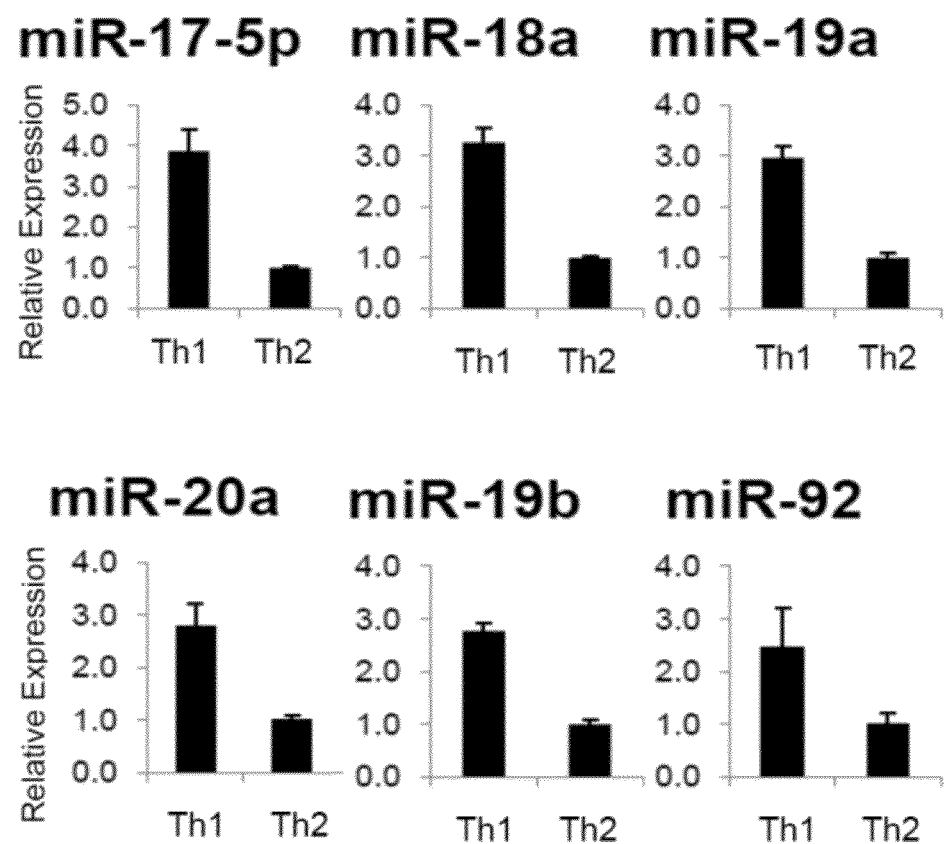
FIG. 2: Enhanced expression of miRs from the miR-17-92 cluster in Th1 cells. Data represent relative expression of mature miRs in Th1 compared with Th2 cells. SNO202 was used as the internal control and $\Delta\Delta C_T$ method was used to examine expression relative to the Th2 cell value. Relative expression is shown for (A) miR-17-92 cluster members or (B) representative paralog cluster members, miR-106a and miR-106b. Error Bars indicate standard deviation of the triplicate samples. Each experiment was repeated at least 3 times. Up-regulation in Th1 vs. Th2 is significant in (A) with p<0.01 for miR-92 and p<0.0001 for all other miRs and in (B) with p<0.001 for miR-106a and p<0.05 for miR106b using the student t test.

This example describes results demonstrating that (i) expression of the miR17-92 cluster is greater in Th1 cells compared to Th2 cells; (ii) the IL-4R/STAT6 signaling pathway regulates expression of miR-17-92; and (iii) over-expression of miR-17-92 in T cells promotes a Th1 phenotype and render cells resistant to AICD.

miR17-92 and its Paralogs are Overexpressed in Th1 Cells Compared with Th2 Cells To identify differentially expressed miRs between Th1 and Th2 cells, miR microarray analysis was performed. From mouse splenic CD4+ T cells, Th1 and Th2 cells were generated as described in Example 1. These T cells exhibited expected cytokine profiles with Th1 cells dominantly producing IFN-γ, but not IL-4, while Th2 cells produced mostly IL-4 (FIG. 1A). Total RNA was extracted from these T cells, and analyzed for differential miR expression by miR microarray for 714 miRs (FIG. 1B). Hierarchical clustering of differentially expressed miRs revealed distinct miR expression profiles between the Th1 and Th2 cells. Eleven of the miRs from the miR-17-92 cluster and its paralogs were expressed at higher levels in Th1 cells than in Th2 cells. Next, the miRs preferentially expressed in Th1 cells were ranked according to the fold difference of expression when compared with Th2 cells (FIG. 1C). Interestingly, members of miRs in the miR-17-92 clusters were identified as the most differentially expressed of all miRs in Th1 cells compared to Th2 cells. Since miR-17-92 clusters appear to be transcribed as single polycistronic transcripts (FIG. 1D), it was expected that all the miRs from the miR-17-92 cluster would be consistently expressed at higher levels in Th1 cells than in Th2 cells, which was confirmed by RT-PCR analysis (FIG. 2A).

The miR-17-92 cluster has 2 paralog clusters: miR-106a-363 and miR-106b-25.

Figure 2B:
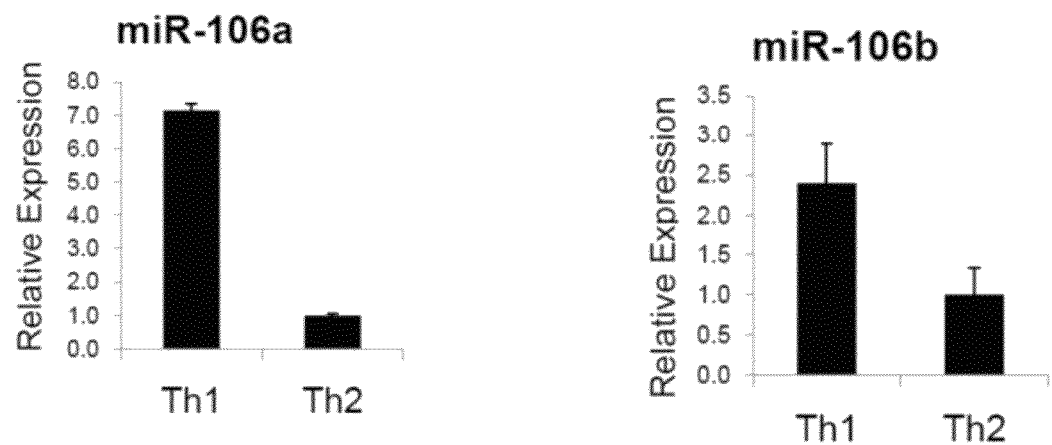

These paralog clusters target similar mRNAs as the miR-17-92 cluster due to high sequence homology (Mendell, *Cell* 2008, 133:217-222). To establish if these paralog miR clusters are also overexpressed in the Th1 vs. Th2 cells, RT-PCR was performed for miRs in each of these clusters. Representative for these paralog clusters are miR-106a and miR106b (FIG. 2B). These data demonstrate that the paralog clusters of miRs were also up-regulated in Th1 cells over Th2.

Figure 3A:
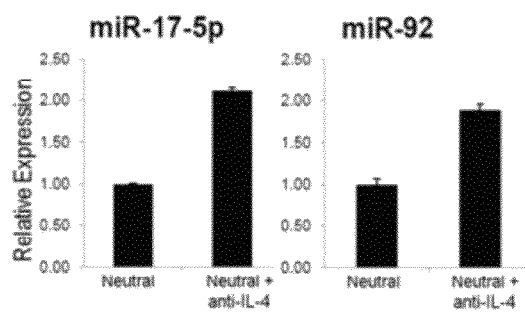
FIG. 3: Modulation of miR-17-92 expression by IL-4 signaling. (A) Immuno-magnetically isolated mouse splenic CD4$^+$ T cells were cultured with 5 µg/ml plated anti-CD3, feeder cells and 100 U/ml hIL-2 ("neutral" condition). Anti-IL-4 (2.5 µg/ml) or isotype control monoclonal antibody (mAb) was added to the appropriate wells and cultured for 5 days prior to extraction of total RNA. Statistical analysis was carried out using the student t test. The blockade of IL-4 significantly up-regulated miR-17-5p and miR-92 (p<0.001 and p<0.005, respectively). (B) CD4$^+$ T cells were cultured with anti-CD3, feeder cells, and hIL-2 and varying amounts of IL-4 for 5 days. Total RNA was extracted and analyzed by RT-PCR for miR-17-5p expression. The dose dependent decrease of miR-17-92 expression was analyzed using post test for linear trend and was significant (p<0.001). (C) Th1 and Th2 cells were induced from splenic CD4$^+$ T cells isolated from either wild-type or STAT6$^{-/-}$ mice. Total RNA was extracted and RT-PCR was performed using specific primers against miR-17-5p and miR-92. Columns represent the mean of triplicates from one of 2 two experiments with similar results, and error bars represent standard deviations. STAT6$^{-/-}$ cells demonstrated significantly higher levels of miR-17-5p and miR-92 compared with wild type (WT) cells in both Th1 and Th2 conditions (p<0.001) using the student t test.
Figure 3B:
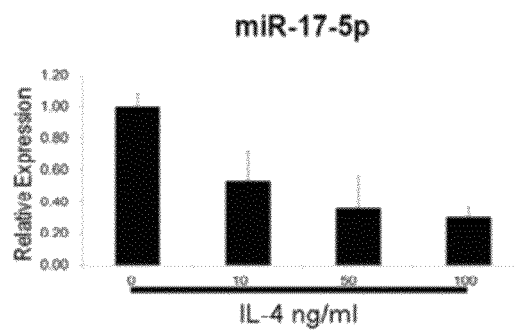

Neutralization of Endogenous IL-4 up-regulates miR-17-92 Cluster miRs in T-Cells In order to identify factors that contribute to the differential expression of miR-17-92 cluster miRs between Th1 and Th2 cells, it was investigated whether a prototypical type-2 inducing cytokine, IL-4, would affect miR-17-92 expression in CD4+ T cells. Neutralization of endogenous IL-4 by specific mAb against IL-4 up-regulated miR-17-92 cluster miRs in CD4+ T cells stimulated with IL-2 without addition of Th1-inducing factors IL-12 or IFN-γ, by approximately 50% (FIG. 3A). The anti-IL-4 mAb also up-regulated miR-17-92 in Th2 culture conditions as well. To determine whether there is an IL-4 dose-dependent suppression of miR-17-92 cluster, CD4+ T cells were treated with increasing doses of IL-4 at 0, 10, 50 or 100 ng/ml and miR-17-5p expression was measured by RT-PCR (FIG. 3B). miR-17-92 suppression was a dose-dependent phenomenon.

Up-regulated miR-17-92 Expression in STAT6-deficient T Cells

Figure 3C:
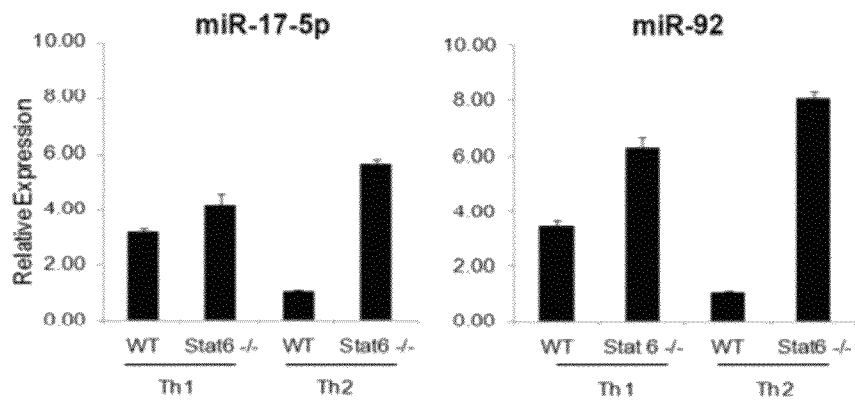

To further elucidate the effect of IL-4 signaling on miR-17-92 cluster expression, CD4+ T cells were cultured under Th1 or Th2 skewing conditions from mice deficient of the critical IL-4 signaling molecule, STAT6 (Sasaki et al., *The Journal of Immunology* 2008, 181:104-108; Eguchi et al., *GeneTher* 2005, 12:733-741). Both Th1 and Th2 cultured cells induced from STAT6-deficient mice showed higher levels of miR-17-5p expression compared with corresponding WT Th cells, suggesting a novel critical role of IL-4R/STAT6-signaling in the down-regulation of miR-17 expression (FIG. 3C).

Suppression of miR-17-92 May Occur in Cancer-Bearing Hosts

Figure 4A:
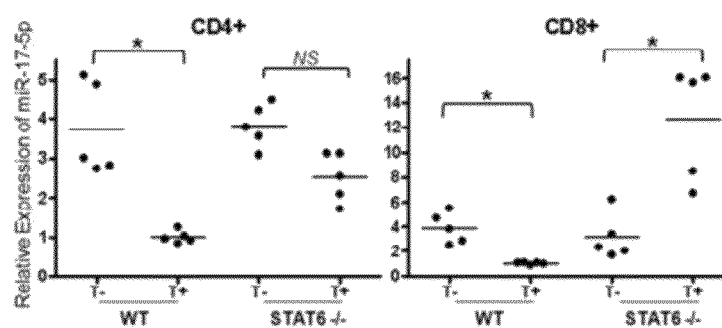
FIG. 4: Tumor bearing conditions down-regulate miR-17-5p expression in T cells. Splenocytes (SPCs) were harvested from C57BL/6 or STAT6$^{-/-}$ mice bearing day 15 subcutaneous B16 melanoma (T+) or control non-tumor bearing mice (T−). (A) CD4$^+$ and CD8$^+$ T cells were isolated by immuno-magnetic bead separation, and evaluated for miR17-5p expression. (B) 1×10$^6$ CD4$^+$ cells from WT mice were briefly stimulated with anti-CD3 mAb for 6 hours. Concentration of IFN-γ secreted in culture media was evaluated by specific enzyme-linked immunosorbent assay (ELISA). (C) CD4$^+$ T cells were isolated from healthy donor-derived peripheral blood mononuclear cells (PBMC) and stimulated with 5 µg/ml plated anti-CD3 feeder cells (irradiated PBMC) and 100 IU/ml hIL-2 in the presence or absence of hIL-4 (10 ng/ml) for 5 days prior to extraction of total RNA. (D) Non-stimulated CD4$^+$ and CD8$^+$ T cells were isolated by immuno-magnetic beads from PBMC derived from healthy donors (n=6) or patients with GBM (n=8) and miR-17-5p expression was analyzed by RT-PCR. Data in (A), (B) and (C) are representative of two identical experiments with similar results. Columns represent the mean of triplicates from a single experiment and error bars represent standard deviation. "*" indicates p<0.01 and "**" indicates p<0.05 between the two groups using the student t test.
Figure 4B:
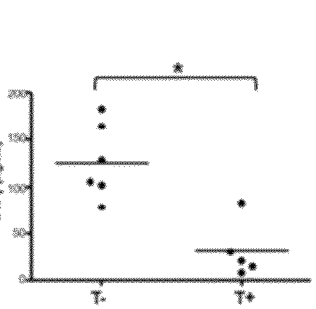

These data led to the hypothesize that suppression of miR-17-92 would occur in cancer-bearing hosts where tumor-derived factors likely promote Th2-skewed immune responses and secretion of IL-4 (Roussel et al., *Clin Exp Immunol* 1996, 105:344-352). Indeed, CD4+ and CD8+ SPCs derived from wild type C57BL/6 mice bearing B16 subcutaneous tumors expressed lower levels of miR-17-5p when compared with those derived from non-tumor bearing mice (FIG. 4A). Interestingly, the tumor bearing condition did not suppress miR-17-5p expression by CD4+ T cells in STAT6−/− mice. Furthermore, CD8+ T cells in STAT6−/− mice demonstrated enhanced levels of miR-17-5p expression when these mice bore B16 tumors compared with non-tumor bearing mice. When wild type CD4+ T cells were stimulated with anti-CD3 mAb in vitro for 24 hours, the CD4+ T cells from tumor-bearing mice produced lower levels of IFN-γ when compared with ones from non-tumor bearing wild type mice (FIG. 4B). These data suggest that tumor-associated immunosuppression may involve the down-regulation of miR-17-92 through a STAT6 dependant pathway.

Figure 4C:
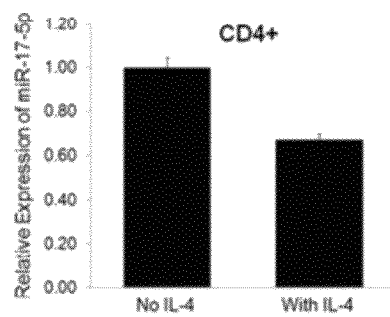
Figure 4D:
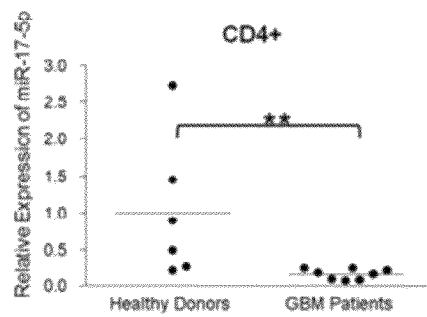

It was next evaluated whether the observed IL-4-mediated and tumor-induced suppression of miR-17-92 are relevant in human T cells. When healthy donor-derived CD4+ T cells were stimulated with rhIL-2, anti-CD3 and anti-CD28 mAbs, consistent with the mouse data, addition of rhIL-4 in the cultures suppressed expression of miR-17-5p (FIG. 4C). Moreover, CD4+ T cells obtained from patients with GBM exhibited significantly decreased levels of miR-17-5p when compared with ones from healthy donors (FIG. 4D). Thus, both IL-4 and GBM-bearing conditions suppress miR-17-5p expression in CD4+ T cells. Although not statistically significant, CD8+ T cells demonstrated a trend towards decreased levels of miR-17-5p expression in GBM patients when compared with healthy donors (FIG. 4D).

Figure 5A:
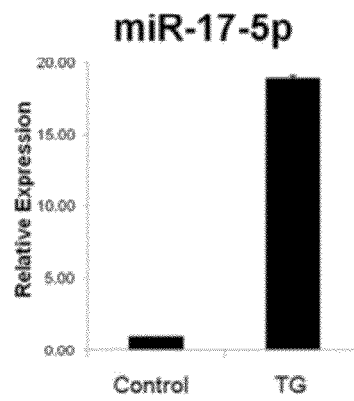
FIG. 5: T cells from miR-17-92 transgenic mice demonstrate enhanced Th1 phenotype. Splenic CD4$^+$ T cells were immuno-magnetically isolated from miR-17-92 transgenic (TG)/TG or control animals. (A) miR-17-5p expression was analyzed in total RNA extracted from these freshly isolated cells. (B) Flow analysis was carried out on these freshly isolated cells for surface expression of CD49d, a subunit composing VLA-4. The grey-shaded region represents CD4$^+$ T cells isolated from control wild type animals and the unshaded region with the solid line represents CD4$^+$ T cells from miR-17-92 TG/TG mice. Dotted lines represent samples stained with isotype control Rat IgG2b. As the background staining with the isotype IgG2b was equally very low in the two cell types, the corresponding histograms are barely distinguishable from each other. (C) Isolated cells were stimulated in Th1 skewing condition for 9 days and 5×10$^6$ cells were then plated in fresh media for 24 hours, at which point supernatant was collected and analyzed for IFN-γ by ELISA. Both in (A) and (C) values in the two groups were statistically different with p<0.01 using the student t test.
Figure 5B:
Figure 5C:
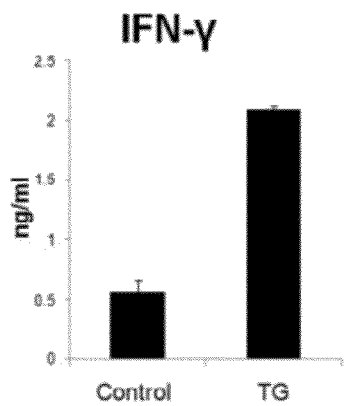

T Cells Derived from miR-17-92 Transgenic Mice Display Enhanced Type-1 Phenotype The data discussed above strongly suggest GBM-associated factors and a type-2 promoting cytokine (IL-4) down-regulate miR-17-92 in T cells. miR-17-92 is expected to play pivotal roles in T cell functions. Experiments were therefore carried out to determine whether ectopic expression of miR-17-92 would promote the type-1 phenotype of T cells. As detailed in Example 1, mice that overexpress miR-17-92 specifically in T cells (miR-17-92 TG/TG) were generated. CD4+ splenocytes were isolated from these mice and the expression of miR-17-5p was evaluated (FIG. 5A). CD4+ cells from TG/TG mice displayed a greater than 15-fold increase in miR-17-p5 expression as compared with controls. These cells also expressed elevated levels of CD49d, which is a subunit of a type-1 T cell marker VLA-4 (FIG. 5B). Although CD49d (also known as α4-integrin) can form heterodimers with both β1 (CD29) and β7 integrins, α4β7 complexes were not expressed by either Th1 cells or Th2 cells, suggesting that CD49d is a suitable surrogate for VLA-4 expression levels (Sasaki et al., *The Journal of Immunology* 2008, 181:104-108; Sasaki et al., *Eur J Immunol* 2008, 38:2865-2873; Zhu et al., *J Transl Med* 2007, 5:10; Sasaki et al., *Cancer Res* 2007, 67:6451-6458). miR-17-92-TG/TG CD4+ cells also demonstrated enhanced ability to produce IFN-γ upon stimulation (FIG. 5C). Similar data were obtained with CD80+ T cells isolated from these TG/TG mice. These findings suggest that miR-17-92 promotes the type-1 phenotype in differentiating T cells.

Figure 6A:
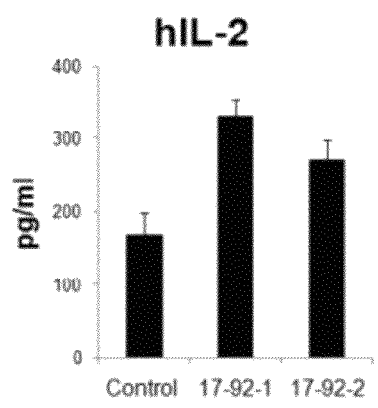
FIG. 6: Ectopic expression of miR-17-92 cluster members in the human Jurkat T cell line confers increased IL-2 production and resistance to AICD. Jurkat cells were transduced by either one of the following pseudotyped lentivirus vectors: 1) control vector encoding green fluorescent protein (GFP); 2) the 17-92-1 expression vector encoding miR-17, miR-18 and miR-19a; or 3) the 17-92-2 expression vector encoding miR-20, miR-19b-1 and miR-92a-1. (A) Transduced Jurkat cells (5×10$^4$) in the triplicate wells were stimulated with phorbol 12-myristate 13-acetate (PMA; 10 ng/ml) and ionomycin (500 nM) overnight and supernatant was harvested and tested for the presence of IL-2 by specific ELISA. The figure shows mean values and standard deviations of the amount of IL-2 released from each group. Statistical analysis was carried out using the student t test, and a significant (p<0.005) increase of IL-2 production was confirmed in both 17-92-1 and the 17-92-2 transduced groups compared with the control group. (B) Transduced Jurkat cells were treated with the activation-induced cell death (AICD) inducing condition (10 µg/ml anti-CD3 mAb) or in complete media (No Tx) for 24 hours. Then, the relative numbers of viable cells were evaluated by 4 hour WST-1 assays. The figure shows mean values and standard deviations of 8 wells/group, each containing 5×10$^5$ cells. For each group, the relative optical density readings at 450 nm of AICD-treated cells compared with control Jurkat cells without AICD-treatment is indicated. "*" indicates p<0.05 between the two groups using student t test.

Ectopic Expression of miR-17-92 Promotes IL-2 Production and Resistance Against Activation-Induced Cell Death (AICD) in Jurkat Cells miR-17-92 is expected to play pivotal roles in T cell survival as well as functions. To evaluate these aspects, Jurkat cells were transduced with lentiviral vectors encoding GFP and either the miR-17-92-1 expression vector encoding miR-17, miR-18 and miR-19a, or the 17-92-2 expression vector encoding miR-20, miR-19b, and miR-92. The control vector encodes GFP, but not miRs. Transduced Jurkat cells were stimulated with PMA and ionomycin overnight before the supernatants were assayed for IL-2 production by ELISA (FIG. 6A). Transduction of either miR-vector promoted IL-2 production in Jurkat cells.

Figure 6B:
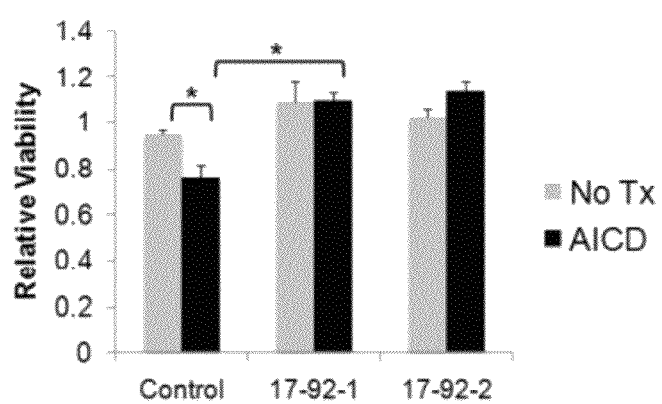

AICD and chemotherapy-induced suppression of T cells represent major obstacles for efficient T cell-based cancer immunotherapy (Kennedy and Celis, *Immunological Reviews* 2008, 222:129-144; Brenner et al., *Critical Reviews in Oncology/Hematology* 2008, 66:52-64). It was next examined whether transfection of Jurkat cells with miR-17-92 renders T cells resistant to AICD. AICD was induced by cultivation of Jurkat cells in the presence of 10 μg/ml anti-CD3 mAb, which is hyper-stimulatory and used as a standard method to induce AICD (Jiang et al., *Clin Exp Med* 2009). As demonstrated in (FIG. 6B), the growth of control Jurkat cells was significantly suppressed by nearly 25% in the AICD inducing condition compared with the same cells with the regular (growth-promoting) dose of anti-CD3 mAb (1 μg/ml). In contrast, the growth of Jurkat cells transduced with either miR-17-92-1 or miR-17-92-2 was not significantly altered by the high dose (10 μg/ml) of anti-CD3 mAb, suggesting that the miR-17-92 transfection confers T cells with substantial resistance against AICD. These findings point to a potential utility for miR-17-92 transfected T cells in cancer immunotherapy.

Summary of Results

Attaining effective tumor immunity is a major goal of modern biologic therapy, limited by the tumor microenvironment and profound regulatory mechanisms limiting T cell and NK cell effectors. It is demonstrated herein that the type-2-skewing tumor microenvironment induces down-regulation of miR-17-92 expression in T cells, thereby hampering anti-tumor T cell responses. It also suggests that development of immunotherapy using miR-17-92-transduced T cells is warranted based on these findings demonstrating that ectopic expression of miR-17-92 in T cells leads to improved type-1 functions, including increased VLA-4 expression and IFN-γ production.

Blockade of endogenous IL-4 by inhibitory mAb or disruption of STAT6 signaling was sufficient to up-regulate miR-17-92 in T cells (FIG. 3). These findings suggest that STAT6 may negatively regulate miR-17-92 expression in T cells. Several transcription factors have been identified that regulate expression of this miR cluster, including the E2 transcription factor (E2F) family members (Woods et al., *J Biol Chem* 2007, 282:2130-2134; Sylvestre et al., *J Biol Chem* 2007, 282:2135-2143), c-Myc (O'Donnell et al., *Nature* 2005, 435:839-843), STAT3 (Brock et al., *Circ Res* 2009, 104:1184-1191), as well as the sonic hedgehog pathway (Northcott et al., *Cancer Res* 2009, 69:3249-3255; Uziel et al., *Proc Natl Acad Sci USA* 2009, 106:2812-2817). With regard to the effects of IL-4/STAT6 signaling on Th1 vs. Th2 functions, the inventors have recently demonstrated that STAT6$^{-/-}$ Th2 cells exhibit Th1 phenotype with increased surface expression of VLA-4 (Sasaki et al., *Journal of Immunotherapy* 2009, 32:793-802). These observations have led to the hypothesis that STAT6-regulated miR-17-92 may contribute to the promotion of type-1 T cell functions.

These findings indicate that the tumor-bearing host down-regulates miR-17-92 in T cells (FIGS. 3 and 4). Interestingly, not only are STAT6$^{-/-}$ T cells resistant to tumor-induced inhibition of miR-17-5p, but CD8+ T cells in tumor bearing STAT6$^{-/-}$ mice exhibited higher levels of miR-17-5p when compared with CD8+ T cells obtained from non-tumor bearing STAT6$^{-/-}$ mice. In addition to IL-4, other tumor-derived factors are likely to be involved in these events.

While tumor bearing mice demonstrated decreased levels of miR-17-92 in both CD4+ and CD8+ cells, human GBM patients exhibited a statistically significant decrease of miR-17-92 in CD4+ cells but not in CD8+ cells (FIG. 4). However, there is a trend towards lower miR-17-92 expression in GBM patient-derived CD8+ cells compared with those obtained from healthy donors. The type-1 vs. type-2 differentiation appears to be more distinct for CD4+ T cells than for CD8+ cells (Ehi et al., *Oncol Rep* 2008, 19:601-607; Tatsumi et al., *Cancer Res* 2003, 63:4481-4489), and this may also be the case for miR-17-92.

Messages encoding proteins that are targeted by miR-17-92 cluster miRs include: E2F1, E2F2, E2F3 (O'Donnell et al., *Nature* 2005, 435:839-843; Brock et al., *Circ Res* 2009, 104:1184-1191), P21 (Inomata et al., *Blood* 2009, 113:396-402), anti-angiogenic thrombospondin-1 and connective tissue growth factor (Dews et al., *Nat Genet.* 2006, 38:1060-1065), proapoptotic Bim, and phosphatase and tensin homolog (PTEN) (Xiao et al., *Nat Immunol* 2008, 9:405-414). These proteins are all involved in cell cycle regulation or apoptotic cell death, further supporting the importance of miR-17-92 cluster in T cell biology. In fact, Bim and PTEN are down-regulated in T cells overexpressing miR-17-92 (Xiao et al., *Nat Immunol* 2008, 9:405-414). Furthermore, TGF-β receptor II (TGFBRII) is one of the established targets of miR-17-92 (Volinia et al., *Proc Natl Acad Sci USA* 2006, 103:2257-2261).

The findings demonstrating increased IFN-γ production from miR-17-92 TG/TG T cells compared with control cells suggest that miR-17-92 promotes the type-1 skewing of T cells (FIGS. 5 and 6C). As miR-17-92 targets hypoxia-inducible factor (HIF)-1a in lung cancer cells (Taguchi et al., *Cancer Res* 2008, 68:5540-5545), enhanced miR-17-92 expression in activated T cells may promote the type-1 function of T cells at least partially through down-regulation of HIF-1α. Although HIF-1 expression provides an important adaptation mechanism of cells to low oxygen tension (Sitkovsky and Lukashev, *Nat Rev Immunol* 2005, 5:712-721; Semenza, *Current Opinion in Genetics & Development* 1998, 8:588-594), it does not appear to be critical for survival of T cells, unlike its apparent role in macrophages (Cramer et al., *Cell* 2003, 112: 645-657). T cells do not depend on HIF-1α for survival to the same degree as macrophages since activated T cells produce ATP by both glycolysis and oxidative phosphorylation (Brand and Hermfisse, *FASEB J* 1997, 11:388-395). Rather, HIF-1α in T cells appears to play an anti-inflammatory and tissue-protecting role by negatively regulating T cell functions (Sitkovsky and Lukashev, *Nat Rev Immunol* 2005, 5:712-721; Neumann et al., *Proc Natl Acad Sci USA* 2005, 102:17071-17076; Eltzschig et al., *Blood* 2004, 104:3986-3992). Indeed, T cell-targeted disruption of HIF-1α leads to increased IFN-γ secretion and/or improved effector functions (Kojima et al., *Proc Natl Acad Sci USA* 2002, 99:2170-2174; Lukashev et al., *J Immunol* 2006, 177:4962-4965; Guo et al., *Int Arch Allergy Immunol* 2009, 149:98-102; Thiel et al., *PLoS One* 2007, 2:e853). Although available data on gene expression profiles in Th1 and Th2 cells do not suggest differential expression of HIF-1α mRNA between these cell populations (Nagai et al., *Int Immunol* 2001, 13:367-376), as is often the case in miR-mediated gene expression regulation, miR-17-92 may still regulate HIF-1α protein expression at post-transcriptional levels. These data collectively suggest that miR-17-92 expression in activated T cells promotes the type-1 function of T cells at least partially through down-regulation of HIF-1α.

The human Jurkat T cell line with ectopic expression of miR-17-92 cluster members demonstrate increased IL-2 production and improved viability following treatment with the AICD condition (FIG. 6). The Jurkat cell line was established from the peripheral blood of a T cell leukemia patient in the 1970s. This cell line is often used to recapitulate what would happen in humans T cells as the line retains many T cell properties, such as CD4, a T cell receptor, and ability to produce IL-2 (Abraham and Weiss, *Nat Rev Immunol* 2004, 4:301-308). For these reasons, Jurkat cells were for the experiments disclosed herein.

miRs in the miR-17-92 clusters are amplified in various tumor types including B cell lymphoma and lung cancer, and promote proliferation and confer anti-apoptotic function in tumors, thereby promoting tumor-progression and functioning as oncogenes (He et al., *Nature* 2005, 435:828-833; Hayashita et al., *Cancer Res* 2005, 65:9628-9632; Matsubara et al., *Oncogene* 2007, 26:6099-6105; Lawrie, *Expert Opin Biol Ther* 2007, 7:1363-1374; Rinaldi et al., *Leuk Lymphoma* 2007, 48:410-412). However, miR-17-92 by itself may not be responsible for oncogenesis as transgenic mice with miR-17-92 overexpressed in lymphocytes develop lymphoproliferative disorder and autoimmunity but not cancer (Xiao et al., *Nat Immunol* 2008, 9:405-414). miR-17-92 may cooperate with other oncogenes to promote the oncogenic process. Transgenic mice overexpressing both miR-17-92 and c-Myc in lymphocytes develop early onset lymphomagenesis disorders (He et al., *Nature* 2005, 435:828-833). On the other hand, knockout studies of the miR-17-92 cluster in mice have demonstrated the importance of this cluster in mammalian biology. While knockout of the miR-17-92 cluster results in immediate post-natal death of all progeny, knockout of either or both the miR-106a or miR-106b clusters are viable without an apparent phenotype (Ventura et al., *Cell* 2008, 132:875-886). However knock out of the miR-17-92 cluster together with miR-106a or 106b cluster results in embryonic lethality (Xiao and Rajewsky, *Cell* 2009, 136:26-36).

During lymphocyte development, miR-17-92 miRs are highly expressed in progenitor cells, with the expression level decreasing 2- to 3-fold following maturation (Xiao et al., *Nat Immunol* 2008, 9:405-414). In addition, the inventors have evaluated relative expression of miR-17-92 in a variety of Th cells as well as naïve CD4$^+$ cells. Naïve CD4$^+$ cells express miR-17-92 at the highest level among the cell populations examined. Albeit lower than that in naïve CD4$^+$ cells, Th1 cells express miR-17-92 at higher levels than T neutral (anti-CD3, feeder cells and IL-2) and Th17 cells, and Th2 cells consistently exhibit the lowest levels of miR-17-92 among the populations tested.

Example 3

Inhibition of Tumor Growth in miR-17-92 TG Mice

Figure 7A:
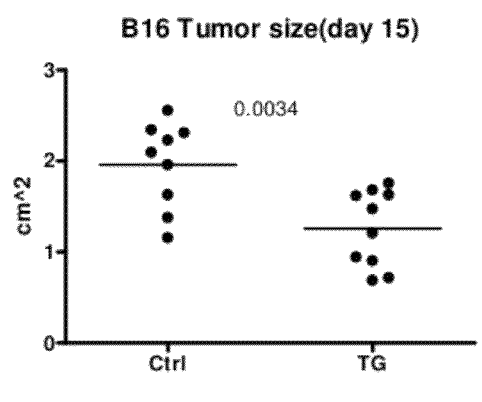
FIG. 7: Inhibition of tumor growth in miR-17-92 TG mice. C57BL/6-background miR-17-92-TG or control Lck-Cre mice received (A) subcutaneous (s.c.) challenge with B16 melanoma cells (1×10$^5$/mouse) and the tumor size was measured on day 15 as square area; or (B) intracranial (i.c.) inoculation of syngeneic GL261 glioma cells (1×10$^5$/mouse) and were followed for symptom-free survival.
Figure 7B:
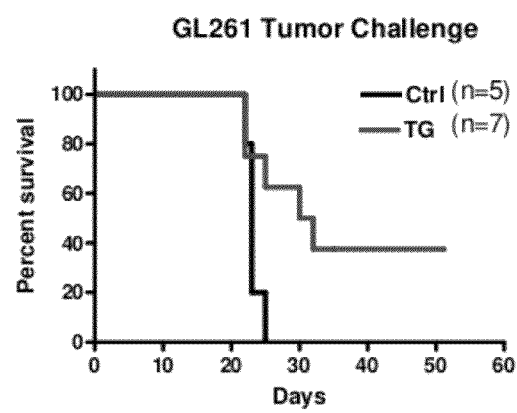

This example supports the methods of engineering tumor antigen (TA)-specific CTLs to express the miR-17-92 cluster that provide potent and durable antitumor activity by potentiating TA-specific type-1 CTL functions. This example describes studies in which C57BL/6-background mice that overexpress miR-17-92 in T cells (miR-17-92-TG mice) or control Lck-Cre mice were challenged with two different tumor systems (FIGS. 7A-7B).

First, mice received s.c. challenge with B16 melanoma cells ($1 \times 10^5$/mouse) and were sacrificed on day 15 following tumor challenge because the size of most tumors exceeded 2 cm$^2$ in control mice. As shown in FIG. 7A, tumors in miR-17-92-TG mice were significantly smaller than those that developed in control mice (p=0.0034 by student-t test, n=9 and 10 for control and miR-17-92-TG mice, respectively).

As a second model, mice received i.c. inoculation of GL261 glioma cells ($1 \times 10^5$/mouse) and were followed for symptom-free survival. As shown in FIG. 7B, all control mice died by day 25 after the tumor inoculation (median 23 days), whereas the survival of miR-17-92-TG mice was significantly longer than that of control mice (median 31 days;

p=0.0426 by Logrank test), and 2 of 7 mice were still alive 50 days following tumor inoculation.

The results of these in vivo studies demonstrate that over-expression of miR-17-92 in T cells significantly inhibits tumor growth and/or tumor induced death.

Example 4 miR-17-92-TG T Cells Infiltrate Gliomas More Intensively than Control T Cells

Figure 8:
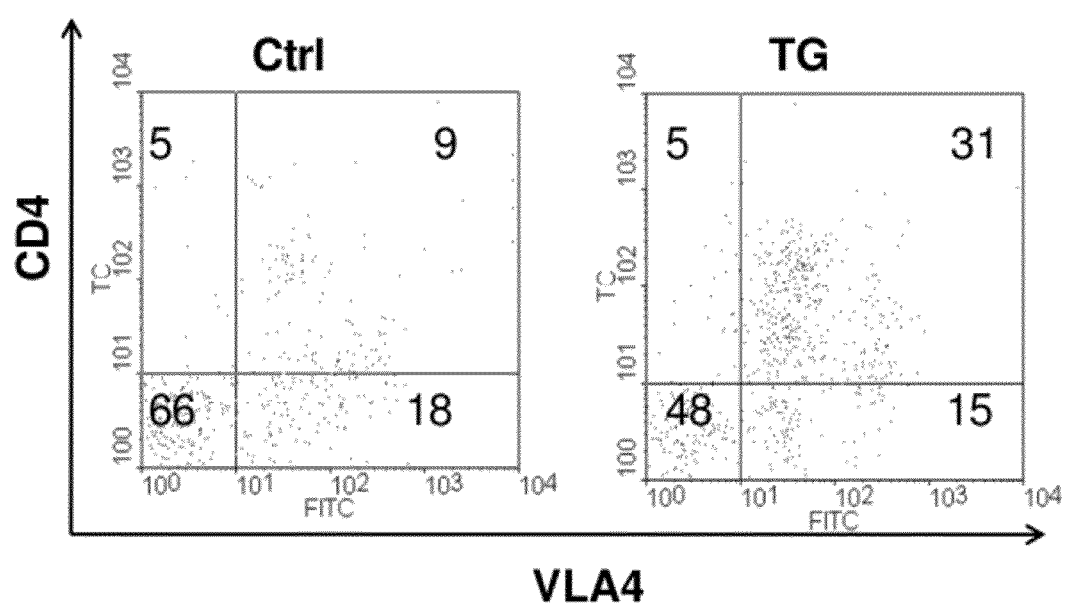
FIG. 8: Transgenic expression of miR-17-92 TG in T cells promotes T cell infiltration in GL261 glioma. C57BL/6-background miR-17-92-TG or control Lck-Cre mice bearing i.c. GL261 glioma (n=4/group) were sacrificed on day 23, and brain infiltrating leukocytes (BILs) were harvested and pooled for the same groups, then subjected to flow-cytometric analyses of CD4$^+$ VLA-4$^+$ cells. Numbers in each histogram indicate percentages of corresponding cells in leukocyte-gated populations.

The glioma experiment described in Example 3 and depicted in FIG. 7B was repeated by challenging miR-17-92-TG or control Lck-Cre mice (n=4/group) with i.c. inoculation of syngeneic GL261 glioma cells, with the exception that these mice were sacrificed on day 23 to evaluate the immunological microenvironment of the glioma sites by flow-cytometric evaluation of brain-infiltrating leukocytes (BILs). As shown in FIG. 8, BILs were stained for T cell marker CD3 as well as VLA-4 as a critical homing receptor to the brain tumor sites (Sasaki et al., *J Immunol* 181:104-108, 2008; Sasaki et al., *Eur J Immunol* 38:2865-2873, 2008; Sasaki et al., *Cancer Res* 67:6451-6458, 2007; Zhu et al., *J Transl Med* 5:10, 2007).

Interestingly, tumors in miR-17-92-TG mice were infiltrated more heavily by $CD3^+VLA-4^+$ cells compared with control mice. Enumeration of $CD3^+VLA-4^+$ cells by multiplying the total number of leukocyte-gated BILs and the percentage of this population revealed $1.3 \times 10^4$/mouse in the control mice compared with $6.4 \times 10^4$/mouse in miR-17-92-TG mice. As transgenic expression of miR-17-92 in miR-17-92-TG mice is restricted in their T cells owing to Lck-Cre system, these results suggest that transgenic expression of miR-17-92 in T cells promotes trafficking of T cells to glioma sites, thereby promoting anti-tumor immunity.

Example 5 miR-17-92 Expression Confers T Cell Resistance to AICD of Primary Mouse T Cells

AICD represents major obstacles for efficient T cell-based cancer immunotherapy. Example 2 describes results in a T cell line (Jurkat) demonstrating that miR-17-92 overexpression confers resistance to AICD. It was next examined whether transgenic miR-17-92 expression confers primary T cells resistant to AICD. AICD was induced by cultivation of miR-17-92 TG Tc1 or control TG Tc1 in the presence of 10 µg/ml anti-CD3 mAb. The number of control Tc1 cells was significantly reduced by nearly 45% in the AICD inducing condition compared with the same cells with the regular (growth-promoting) dose of anti-CD3 mAb (1 µg/ml). In contrast, the number of T cells transgenic with miR-17-92 was not significantly altered by the high dose (10 µg/ml) of anti-CD3 mAb, suggesting that the miR-17-92 transfection confers T cells with substantial resistance against AICD.

Example 6

T cells Over-Expressing miR17-92 for Cancer Immunotherapy

This example illustrates methods to further demonstrate miR-17-19b over-expression can promote proliferation of adoptively-transferred tumor-antigen specific T cells in situ and exert potent anti-tumor response in vivo. This method also provides an example of how to perform cancer immunotherapy.

The efficiency of T cell-adoptive transfer therapy largely depends upon the persistence and proliferation of transferred T cells in vivo, and this has been the rate-limiting step for development of successful immunotherapy. Tumor-induced type-2 deviation and other immuno-suppression mechanisms appear to induce inactivation and death of anti-tumor T cells. In order to sustain effective proliferation of adoptively-transferred tumor-specific Tc1 cells, genetically engineered miR-17-19b over-expressing Tc1 and Tc2 are generated and adoptively transferred into intracranial GL261-bearing mice.

Using a Hamilton syringe, $1 \times 10^5$ GL261 glioma cells are stereotactically injected through an entry site at the bregma, 3 mm to the right of sagittal suture and 4 mm below the surface of the skull of anesthetized mice using a stereotactic frame (Kopf). The miR-17 or control backbone vector are infected into Tc1 and Tc2 cells. On day 10, five mice per group receive an i.v. injection with $2 \times 10^7$ miR-17 or control vector-transfected Tc1 cells that have been cultured for 9 days with 100 U/ml of hIL-2. Mice are closely monitored for any neurological signs, or any signs of weakness or malaise, which are considered to be endpoints. When endpoints are observed, the mice are sacrificed. The survival of mice is analyzed using the Kaplan Mayer method. As a means of immunological monitoring, blood is drawn from mice treated with engineered Tc1 cells, then serum IFN-γ and IL-4 levels are assessed by ELISA.

In another set of experiments, mice are given BrdU in the drinking water for 5 days after i.v. transfer of engineered Tc1 cells. At day 6 after adoptive-transfer, mice are sacrificed and BILs are isolated as described previously (Nishimura et al., *Cancer Res.* 66:4478-4487, 2006). BILs are stained extracellularly with PE-gp$100_{25-33}^-$H-2D$^b$-tetramer, permeabilized using the CYTOFIX/CYTOPERM™ kit (BD Biosciences), and stained with FITC-anti-BrdU mAb. It is anticipated that miR-17-19b-transfected Tc1 cells will demonstrate higher proliferation levels than control-transfected Tc1 cells after encountering the tumor-antigens in situ.

To eliminate concerns for development of lymphoma by the stable gene-transfer of miR-17, normal tumor-free C57BL/6 mice (5 mice/group) receive i.v. transfer of $2 \times 10^7$ miR-17- or control-transfected Tc1 cells per mouse. Mice have blood (50 µl) drawn from the tail vein, and are then monitored for the presence of leukemia by blood smear analysis at 5, 10, 20 and 40 weeks after the adoptive-transfer. Mice are also observed for any changes in physical appearance and demeanor including weakness, hunch back, weight-loss and general malaise. Mice demonstrating any of the signs above, or those surviving longer than 120 days, are sacrificed. Lymphoid (cervical, axillary, and inguinal, mesenteric lymphnodes, spleen) and non-lymphoid (brain, kidney, liver, bone-marrow, intestine) organs are harvested. To this end, hematoxylin and eosin (H&E) staining is employed to examine the presence of malignancies.

The treatment methods described herein can easily be adapted for other species or subjects, such as humans.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

The invention claimed is:

1. A method of treating a subject with a glioma, comprising (i) selecting a subject with the glioma; and (ii) administering to the subject an isolated glioma-associated antigen-specific cytotoxic T cell comprising a heterologous nucleic acid molecule encoding a miR-17-92 transcript, thereby treating the subject with the glioma.

2. The method of claim 1, wherein the heterologous nucleic acid molecule comprises a vector.

3. The method of claim 2, wherein the vector is a plasmid vector.

4. The method of claim 2, wherein the vector is a viral vector.

5. The method of claim 4, wherein the viral vector is a lentiviral vector.

6. The method of claim 1, wherein the miR-17-92 transcript is a human miR-17-92 transcript.

7. The method of claim 1, wherein the isolated glioma-associated antigen-specific cytotoxic T cell expresses a chimeric antigen receptor that specifically binds the glioma-associated antigen.

8. The method of claim 1, wherein the isolated glioma-associated antigen-specific cytotoxic T cell expresses an antibody or fragment thereof that specifically binds the glioma-associated antigen.

9. A method of treating a subject with a glioma, comprising:

(i) selecting a subject with the glioma;

(ii) isolating T cells from the subject, wherein the T cells comprise glioma-associated antigen-specific T cells;

(iii) transfecting the isolated glioma-associated antigen-specific T cells with a heterologous nucleic acid molecule encoding the miR-17-92 transcript; and (iv) administering to the subject the isolated glioma-associated antigen-specific T cells transfected with the miR-17-92 transcript, thereby treating the subject with the glioma.

10. A method of treating a subject with a glioma, comprising:

(i) selecting a subject with the glioma;

(ii) isolating T cells from the subject, (iii) engineering the T cells to express a chimeric antigen receptor, or an antibody or fragment thereof, that specifically binds a glioma-associated antigen to produce isolated glioma-associated antigen-specific T cells;

(iv) transfecting the isolated glioma-associated antigen-specific T cells with a heterologous nucleic acid molecule encoding the miR-17-92 transcript; and (v) administering to the subject the isolated glioma-associated antigen-specific T cells transfected with the miR-17-92 transcript, thereby treating the subject with the glioma.

11. The method of claim 10, wherein the isolated T cells are engineered to express a chimeric antigen receptor that specifically binds a glioma-associated antigen.

12. The method of claim 10, wherein the isolated T cells are engineered to express an antibody or fragment thereof that specifically binds a glioma-associated antigen.

* * * * *

UNITED STATES PATENT AND TRADEMARK OFFICE
CERTIFICATE OF CORRECTION

PATENT NO. : 8,486,911 B2  
APPLICATION NO. : 13/568457  
DATED : July 16, 2013  
INVENTOR(S) : Okada et al.

It is certified that error appears in the above-identified patent and that said Letters Patent is hereby corrected as shown below:

In the Specification:

Column 2, line 3, "That et al." should read --Thai et al.--

Column 6, line 11, "STATE" should read --STAT6--

Column 15, line 14, "let-71" should read --let-7i--

Column 17, line 58, "STATE" should read --STAT6--

Column 18, line 11, "E is et al." should read --Eis et al.--

Column 18, line 25, "That et al." should read --Thai et al.--

Column 25, line 44, "STATE" should read --STAT6--

Column 26, line 66, "$AAC_T$" should read --$\Delta\Delta C_T$--

Column 28, line 45, "STATE" should read --STAT6--

Column 29, line 47, "$CD80^+$" should read --$CD8^+$--

Column 31, line 25, "(HIF)-1a" should read --(HIF)-1$\alpha$--

Signed and Sealed this  
Nineteenth Day of November, 2013

Teresa Stanek Rea  
*Deputy Director of the United States Patent and Trademark Office*

SEQUENCE LISTING

```
<160> NUMBER OF SEQ ID NOS: 26

<210> SEQ ID NO 1
<211> LENGTH: 84
<212> TYPE: RNA
<213> ORGANISM: Homo sapiens

<400> SEQUENCE: 1
gucagaauaa ugucaaagug cuuacagugc agguagugau augugcaucu acugcaguga        60
aggcacuugu agcauuaugg ugac                                              84

<210> SEQ ID NO 2
<211> LENGTH: 23
<212> TYPE: RNA
<213> ORGANISM: Homo sapiens

<400> SEQUENCE: 2
caaagugcuu acagugcagg uag                                               23

<210> SEQ ID NO 3
<211> LENGTH: 22
<212> TYPE: RNA
<213> ORGANISM: Homo sapiens

<400> SEQUENCE: 3
acugcaguga aggcacuugu ag                                                22

<210> SEQ ID NO 4
<211> LENGTH: 84
<212> TYPE: RNA
<213> ORGANISM: Mus musculus

<400> SEQUENCE: 4
gucagaauaa ugucaaagug cuuacagugc agguagugau gugugcaucu acugcaguga        60
gggcacuugu agcauuaugc ugac                                              84

<210> SEQ ID NO 5
<211> LENGTH: 23
<212> TYPE: RNA
<213> ORGANISM: Mus musculus

<400> SEQUENCE: 5
caaagugcuu acagugcagg uag                                               23

<210> SEQ ID NO 6
<211> LENGTH: 22
<212> TYPE: RNA
<213> ORGANISM: Mus musculus

<400> SEQUENCE: 6
acugcaguga gggcacuugu ag                                                22

<210> SEQ ID NO 7
<211> LENGTH: 71
<212> TYPE: RNA
<213> ORGANISM: Homo sapiens

<400> SEQUENCE: 7
uguucuaagg ugcaucuagu gcagauagug aaguagauua gcaucuacug cccuaagugc        60
uccuucuggc a                                                            71
```

```
<210> SEQ ID NO 8
<211> LENGTH: 23
<212> TYPE: RNA
<213> ORGANISM: Homo sapiens

<400> SEQUENCE: 8
uaaggugcau cuagugcaga uag                                                 23

<210> SEQ ID NO 9
<211> LENGTH: 96
<212> TYPE: RNA
<213> ORGANISM: Mus musculus

<400> SEQUENCE: 9
ugcgugcuuu uuguucuaag gugcaucuag ugcagauagu gaaguagacu agcaucuacu         60
gcccuaagug cuccuucugg cauaagaagu uauguc                                   96

<210> SEQ ID NO 10
<211> LENGTH: 23
<212> TYPE: RNA
<213> ORGANISM: Mus musculus

<400> SEQUENCE: 10
uaaggugcau cuagugcaga uag                                                 23

<210> SEQ ID NO 11
<211> LENGTH: 82
<212> TYPE: RNA
<213> ORGANISM: Homo sapiens

<400> SEQUENCE: 11 gcagccucu guuaguuuug cauaguugca cuacaagaag aauguaguug ugcaaaucua          60
ugcaaaacug augguggccu gc                                                  82

<210> SEQ ID NO 12
<211> LENGTH: 23
<212> TYPE: RNA
<213> ORGANISM: Homo sapiens

<400> SEQUENCE: 12
ugugcaaauc uaugcaaaac uga                                                 23

<210> SEQ ID NO 13
<211> LENGTH: 82
<212> TYPE: RNA
<213> ORGANISM: Mus musculus

<400> SEQUENCE: 13
gcagcccucu guuaguuuug cauaguugca cuacaagaag aauguaguug ugcaaaucua         60
ugcaaaacug augguggccu gc                                                  82

<210> SEQ ID NO 14
<211> LENGTH: 23
<212> TYPE: RNA
<213> ORGANISM: Mus musculus

<400> SEQUENCE: 14
ugugcaaauc uaugcaaaac uga                                                 23

<210> SEQ ID NO 15
<211> LENGTH: 71
<212> TYPE: RNA
```

<213> ORGANISM: Homo sapiens

<400> SEQUENCE: 15
guagcacuaa agugcuuaua gugcagguag uguuuaguua ucuacugcau uaugagcacu    60
uaaaguacug c                                                         71

<210> SEQ ID NO 16
<211> LENGTH: 23
<212> TYPE: RNA
<213> ORGANISM: Homo sapiens

<400> SEQUENCE: 16
uaaagugcuu auagugcagg uag                                            23

<210> SEQ ID NO 17
<211> LENGTH: 107
<212> TYPE: RNA
<213> ORGANISM: Mus musculus

<400> SEQUENCE: 17
gugugaugug acagcuucug uagcacuaaa gugcuuauag ugcagguagu guguagccau    60
cuacugcauu acgagcacuu aaaguacugc cagcuguaga acuccag                 107

<210> SEQ ID NO 18
<211> LENGTH: 23
<212> TYPE: RNA
<213> ORGANISM: Mus musculus

<400> SEQUENCE: 18
uaaagugcuu auagugcagg uag                                            23

<210> SEQ ID NO 19
<211> LENGTH: 87
<212> TYPE: RNA
<213> ORGANISM: Homo sapiens

<400> SEQUENCE: 19
cacuguucua ugguuaguuu ugcagguuug cauccagcug ugugauauuc ugcugugcaa    60
auccaugcaa aacugacugu gguagug                                        87

<210> SEQ ID NO 20
<211> LENGTH: 23
<212> TYPE: RNA
<213> ORGANISM: Homo sapiens

<400> SEQUENCE: 20
ugugcaaauc caugcaaaac uga                                            23

<210> SEQ ID NO 21
<211> LENGTH: 87
<212> TYPE: RNA
<213> ORGANISM: Mus musculus

<400> SEQUENCE: 21
cacuggucua ugguuaguuu ugcagguuug cauccagcug uauaauauuc ugcugugcaa    60
auccaugcaa aacugacugu gguggug                                        87

<210> SEQ ID NO 22
<211> LENGTH: 23
<212> TYPE: RNA
<213> ORGANISM: Mus musculus

```
<400> SEQUENCE: 22
ugugcaaauc caugcaaaac uga                                           23

<210> SEQ ID NO 23
<211> LENGTH: 78
<212> TYPE: RNA
<213> ORGANISM: Homo sapiens

<400> SEQUENCE: 23
cuuucuacac agguugggau cgguugcaau gcuguguuuc uguaugguau ugcacuuguc   60
ccggccuguu gaguuugg                                                 78

<210> SEQ ID NO 24
<211> LENGTH: 22
<212> TYPE: RNA
<213> ORGANISM: Homo sapiens

<400> SEQUENCE: 24
uauugcacuu gucccggccu gu                                            22

<210> SEQ ID NO 25
<211> LENGTH: 80
<212> TYPE: RNA
<213> ORGANISM: Mus musculus

<400> SEQUENCE: 25
cuuucuacac agguugggau uugucgcaau gcuguguuuc ucuguauggu auugcacuug   60
ucccggccug uugaguuugg                                               80

<210> SEQ ID NO 26
<211> LENGTH: 21
<212> TYPE: RNA
<213> ORGANISM: Mus musculus

<400> SEQUENCE: 26
uauugcacuu gucccggccu g                                             21
```